United States Patent [19]
Cox et al.

[11] Patent Number: 5,587,157
[45] Date of Patent: *Dec. 24, 1996

[54] STABILIZATION OF BIOWASTES

[76] Inventors: James P. Cox; Robert W. Duffy Cox, both of 246 E. Bartlett Rd., Lynden, Wash. 98264

[*] Notice: The term of this patent shall not extend beyond the expiration date of Pat. No. 5,352,444.

[21] Appl. No.: 474,329

[22] Filed: Jun. 7, 1995

Related U.S. Application Data

[63] Continuation-in-part of Ser. No. 287,183, Aug. 8, 1994, abandoned, which is a continuation of Ser. No. 886,417, May 19, 1992, Pat. No. 5,352,444.

[51] Int. Cl.$^6$ .................................................. A61L 11/00
[52] U.S. Cl. ...................... 424/76.5; 424/76.6; 424/76.8; 424/616; 424/618; 424/630; 424/632; 424/637; 424/639; 424/641; 424/688; 424/690; 514/693; 514/699; 514/703; 514/705; 252/175; 252/180; 252/181
[58] Field of Search .................................. 424/76.5, 76.6, 424/76.7, 76.8, 76.2, 76.21, 76.4, 617, 616, 618, 630, 637, 632, 639, 641, 682, 688, 690; 514/693, 699, 703, 705; 252/175, 180, 181

[56] References Cited

U.S. PATENT DOCUMENTS

| | | |
|---|---|---|
| 145,433 | 12/1873 | Lee et al. . |
| 2,459,896 | 1/1949 | Schwarz . |
| 2,546,898 | 3/1951 | Vande Mark . |
| 2,768,958 | 10/1956 | Stewart et al. . |
| 3,092,552 | 6/1963 | Romans . |
| 3,230,137 | 1/1966 | Ellison . |
| 3,314,745 | 4/1967 | Krotinger et al. . |
| 3,459,852 | 8/1969 | Roehm . |
| 3,509,254 | 4/1970 | Krotinger, Jr. et al. . |
| 3,650,968 | 3/1972 | Hoffman et al. . |
| 3,769,206 | 10/1973 | Brown et al. . |
| 3,785,971 | 1/1974 | Halley . |
| 3,819,516 | 6/1974 | Murchison et al. . |
| 3,966,450 | 6/1976 | O'Neill et al. . |
| 3,989,498 | 11/1976 | Cox . |
| 4,160,656 | 7/1979 | Jukermann . |
| 4,446,031 | 5/1984 | List . |
| 4,448,750 | 5/1984 | Fuesting . |
| 4,477,357 | 10/1984 | Sittenfield . |
| 4,501,668 | 2/1985 | Merk et al. . |
| 4,511,552 | 4/1985 | Cox . |
| 4,608,247 | 8/1986 | Heinig, Jr. . |
| 4,680,127 | 7/1987 | Edmondson . |
| 4,744,904 | 5/1988 | McAninch et al. . |
| 4,752,620 | 6/1988 | Roberts . |
| 4,761,159 | 8/1988 | Knox . |
| 4,816,220 | 3/1989 | Roychowdhury . |
| 4,861,482 | 8/1989 | Frankenberger, Jr. et al. . |
| 4,861,484 | 8/1989 | Lichtin et al. . |
| 4,891,215 | 1/1990 | Kato . |
| 4,902,408 | 2/1990 | Reichert et al. . |
| 4,909,849 | 3/1990 | Funderburk . |
| 4,915,939 | 4/1990 | Iwahashi . |
| 4,923,619 | 5/1990 | Legros . |
| 4,931,192 | 6/1990 | Covington et al. . |
| 4,952,242 | 8/1990 | Earp . |
| 4,956,183 | 9/1990 | Miki et al. . |
| 4,992,213 | 2/1991 | Mallett et al. . |
| 5,045,288 | 2/1991 | Raupp et al. . |
| 5,051,192 | 9/1991 | Charlier . |
| 5,071,622 | 12/1991 | Dunson, Jr. . |
| 5,079,000 | 1/1992 | Takahashi et al. . |
| 5,089,141 | 2/1992 | Murphy . |
| 5,096,600 | 3/1992 | Hoch . |
| 5,137,687 | 8/1992 | Dunson, Jr. . |
| 5,141,647 | 8/1992 | Bhadra . |

FOREIGN PATENT DOCUMENTS

| | | |
|---|---|---|
| 1233120 | 2/1988 | Canada . |
| 1258641 | 8/1989 | Canada . |

*Primary Examiner*—Neil McCarthy
*Attorney, Agent, or Firm*—Christensen O'Connor Johnson & Kindness PLLC

[57] ABSTRACT

Biowaste treatment agents for treating biowastes in a manner which: (a) keeps noxious and toxic substances from being released from the biowaste, and (b) neutralizes such substances released during the course of stabilizing the biowaste. The treatment agents include a surfactant in an amount of from 1.0 to 99 percent of the treatment agent, a metal component in an amount from 0.5 to 85 percent of the treatment agent, the metal component including a source of zinc, or copper, or a combination of copper with aluminum or iron, and an aldehyde in an amount from 0.1 to 80 percent of the treatment agent.

54 Claims, No Drawings

STABILIZATION OF BIOWASTES

RELATED APPLICATIONS

This application is a continuation-in-part of application Ser. No. 08/287,183 filed Aug. 8, 1994, abandoned, entitled "Stabilization of Biowastes", which is a continuation of application Ser. No. 07/886,417 filed May 19, 1992, entitled "Stabilization of Biowastes", which issued as U.S. Pat. No. 5,352,444 on Oct. 4, 1994.

TECHNICAL FIELD OF THE INVENTION

In one aspect, the present invention relates to novel methods for stabilizing biowastes and to polyfunctional complexes for accomplishing this objective.

In another aspect the present invention relates to methods and complexes as just characterized which simplify the treatment of biowastes; make safer, protect and improve the environment; and increase processing capacity and the potential and conserved values of processed biowastes as end products.

BACKGROUND

Disposing of and effectively treating biowastes is an increasingly difficult problem.

The abundant open dumping space of yesterday is now probably someone's backyard. The sites now left are surrounded by someone's air, living, and working spaces and located above someone's drinking water. Everyone, it seems, wants waste in someone else's back yard.

Earth's capacity to absorb and civilization's ability to ignore waste behind a defense of rhetoric rather than action is very nearly at an end.

The axioms, sometimes self-serving, sometimes in hysterical response, that "dilution is the solution to pollution" and at the other extreme—"compaction is the action of satisfaction"—are foundations of heretofore employed waste management techniques. These approaches completely fail to take into consideration the simple fact that the problem of waste is not going to go away on its own accord. Endlessly diluting, compacting, transporting, storing, transmutating or apportioning waste to air, earth and water merely prolongs but makes more certain the ultimate reckoning.

One widely employed solution to the waste disposal problem is incineration of the offending material; another is controlled disposal and/or treatment of the waste in a digester, sanitary landfill, lagoon, compost pile, or the like.

Incineration is of limited value. Capital costs of the equipment required to incinerate all of the wastes generated in a metropolitan or other populous area is prohibitive. Los Angeles, as one example, is reported to generate 500,000 tons of solid waste daily. Incineration is also only a partial solution because non-combustible solids must often be sorted out and otherwise disposed of prior to incineration. Furthermore, complex and noxious emissions generated by incineration are difficult and expensive to control; and the solids generated in an incinerator (and often in an incinerator's stack gas scrubber) are wastes that must be transported to a landfill or other disposal site and stored. The location of acceptable sites for incinerators—especially those intended to accommodate body parts and other perhaps diseased biological wastes—is also a significant problem.

Because of the foregoing and other problems, landfills are still most often employed for solid waste disposal. Like incineration, this approach is not free of significant problems such as siting and the emission of noxious offgases including odorous and inodorous but toxic volatile compounds (VC's). Other problems associated with the disposal of solid wastes in landfills include: the formation of toxic, often highly corrosive leachates; the sheer bulk of the waste; and the control of disease vectors including insects; birds (sea gulls are now being observed in number in the Great Plains); rodents; and other animals such as raccoons, coyotes and the like. Also of concern is the loss of valuable raw material potentials such as plant and other nutrients found in many biological wastes.

Problems of the character discussed above are also appurtenant to many other waste generating and processing operations—composting processes, sewage digesters and lagoons, hospitals, septic tanks, feed lots, slaughterhouses, dairy herds and poultry flocks to name but a few.

These problems also exist in the collection, storage, and movement of biowastes from one point to another. Biochemical effluvia; bacteriologically contaminated garbage bags, cans, and dumpsters; and equally miasmatic garbage trucks, scows, sewer lines and other forms of waste transport prevail; and corrosive, toxic leachates are commonly present.

The same problems exist in the home, in institutions and elsewhere. Unpleasant and toxic volatile compounds evolved from biological wastes which are often contaminated with disease microorganisms are found on airplanes, buses, trains, and boats; in hospitals, nursing homes, restaurants, domestic bathrooms, kitchens and yards. In the home and elsewhere, carpets and other furnishings soiled by such biological wastes as vomit, animal feces, spoiled foods and urine also pose a problem, especially from the viewpoint of the noxious and toxic volatile organic and inorganic compounds they emit.

Extreme and expensive, yet only partially effective, measures are all that are currently available to deal with the VC and disease potential problems described above. For example, governmental regulations commonly require that the active site at a landfill be covered with six or more inches of dirt after each day's operations to seal in volatiles and to form a physical barrier which will keep disease vectors from contaminated wastes. As much as possible of this dirt is then removed the next working day, more waste is added, and the process is repeated.

Covering an irregular biowaste and trash surface with a layer of the requisite depth may be beyond the capability of even a conscientious heavy equipment operator, especially under adverse conditions where only a gluey clay or frozen soil may be all that is available. This approach cannot be employed when it is needed most—during prime daylight and working hours. Furthermore, it has the disadvantage of filling up landfills with dirt instead of wastes. Landfill sites are expensive; and communities, if not entire nations, are running out of sites to which their waste products can affordably be transported.

Other covers—tarpaulins and nets—are occasionally employed instead of dirt. Expensive, inconvenient and filthy from continued reuse, these covers are difficult to roll out and roll up each day. They do not last very long, are only somewhat effective and are more an indication of the seriousness of the problem than a solution to it. Like the dirt cover, the net or tarp offers no protection against or neutralization of VC's and disease vectors during working hours. Nets and tarps also become contaminated with septic liquids in or generated by decomposition of the biowaste. Nets simply add another site attractive to pests and disease vectors. Moreover, workers required to handle septic nets and tarps are at risk while the cost of landfill waste disposal is increased. Finally, nets and tarps, like dirt, become an additional waste disposal burden as they must ultimately be absorbed into the landfill.

Leachates pose a very significant environmental problem. Prevalent and widely publicized are the contamination of water tables and nearby streams, lakes and other bodies of water with leachates from landfills.

In newer landfills, the approach to solving the leachate problem has been to place an impervious polymeric liner in a basin or depression at the active site and dump the waste onto the liner. Leachates are drained from the liner into pools or ponds adjacent the landfill. These liquids are extremely noxious and toxic, a result mostly of the anaerobic processes dominant in a fill. The collected leachates are in most circumstances simply hauled away from the landfill and incinerated.

Commonly associated with these noisome leachates are also deleterious volatile organic compounds (VC's) and equally offensive inorganic gases and vapors. Profiles of the VC's commonly associated with leachates are very complex; but many noxious and toxic, gaseous sulphur and nitrogen compounds are invariably present. Leachates collected in landfill ponds and lagoons are accordingly a major source of atmospheric pollution.

Sewage treatment and other waste processing plants commonly employ more permanent leachate containments such as concrete sludge basins and dissolved air flotation cells, approaches not practical for landfills or for other disposal sites such as agricultural lagoons. Transport and incineration of leachates is expensive and merely serves to concentrate the noxious elements into more subtle but no less deadly oxidation products disseminated without treatment into the atmosphere.

In many circumstances, plastic bags with twist ties, containers with tight fitting lids and the like are employed to contain refuse, offgases and exuded liquids and to protect biowastes from pests and insects and other disease vectors with varying degrees of success. Bags and other containers only become a part of and do not solve the waste disposal problem because the containment does not reduce the amount of solid or liquid waste or offgases but simply stores these materials until the seal or barrier is broken in the collection, handling, disposal and other processing of the waste. Moreover, the breakdown of the stored waste by anaerobic processes can often proceed rapidly in the low oxygen environment of a waste storage container. It is generally accepted that anaerobic processes generate more noxious and toxic byproducts than aerobic processes do. So, to some extent, the solid waste disposal problem is ultimately worsened by use of storage containers. Isolating biowastes for handling and transportation to a disposal site is important but does not solve, only increases, the problems encountered at the waste disposal site.

Biowastes are collected and moved from the collection point to collection stations, then to the treatment and/or disposal site in or through such diverse receptacles as toilets, sewage pipes, the above-discussed plastic bags and garbage cans, and garbage trucks, to name only a few. Non-disposable waste collection and transportation containers including toilets, bedpans, garbage cans, dumpsters and the like can be cleaned to remove waste materials, a procedure which inherently minimizes the spread of these materials throughout the environment. Often employed for cleaning are aqueous solutions of commercial surfactants. If done properly, this approach is effective. However, it has the disadvantage of generating waste laden water, which in itself poses a significant waste disposal problem. Furthermore, in the collection, storage and transportation of biowastes, the common approach is to handle solid biowastes and liquid leachates together. Leaks and spillage and contamination of rolling stock are obvious and important drawbacks of this approach.

Aside from those discussed above, the disposal of biowastes has associated therewith the problem of controlling offensive odors emitted from the waste as it undergoes a variety of chemical reactions. Complexes commonly but inaccurately described as deodorants and usually comprised of volatile organic compounds have been used in attempts to compete with ubiquitous, noxious and toxic volatiles emitted from organic wastes. So-called deodorant bathroom sprays are widely available. And, at some landfills, the covering of the active site with a net at the close of each working day may be followed by the application of an aromatic complex to mediate the olfactory effects of malodorous volatile compounds.

The use of so-called deodorants for the purposes just described is at best of only limited effectiveness. Deodorants do not neutralize the inodorous but noxious volatile compounds commonly associated with malodors, and they deal with the malodor problem only through the questionable phenomenon of masking the offensive odor with a more acceptable one. Deodorants are expensive, tend to have a very limited if any real effectiveness and actually contribute to the problem by adding additional volatile compounds to those already existent in the problem area. Many biowastes contain significant concentrations of constituents with significant nitrogen, sulfur and other nutrient values. These potentially economically important constituents are routinely lost from biowastes because there is no practical process for preventing the loss of these values by volatization.

Instead, efforts have been limited to recovering products with nutritional and other values from the non-volatile components of biowastes. Among the traditional techniques and systems employed to treat and recover such products are digesters for sewage; dissolved air flotation cells for food and other process wastes; drying of fermentation byproducts, grains, and spent microorganisms; spray drying of whey; the drying or homogenizing of manure and fish into fertilizers; agricultural field spraying of livestock wastes; the recovery of pulps from the paper and vegetable and fruit processing industries; the manufacture of products such as particle board from wood and plant wastes and particles; offal rendering and composting.

One of the most valuable constituents of many biowastes is the water in which the biowaste solids are carried. Water is in very short supply in many regions of the world and is expensive. Currently, there are no viable methods for recovering and recycling this water, even for secondary (non-consumption) uses such as washdown; irrigation and operation of boilers, condensers, and cooling towers. Obviously lacking in waste disposal is a recovery technique which would be of considerable economic and other value to hard pressed and water short industries and to agriculturists.

With the exception of rendering, processes for recovering values from biowastes are essentially designed for controlling, handling and disposing of biowaste at as little cost as possible. The value of products actually recovered is very small compared to the product potential. Salvage processes do nothing to protect biowastes prior to or during processing; and they hasten evolution of volatiles, yielding products only after the majority of the damage to the original product and to the environment has been done.

Typical of the salvage processes in widespread use is composting. Composting has the drawback that it is a lengthy process—taking months to a year or more—, and space must be found for the compost pile for this extended period of time. Furthermore, the gases "belched off" as the compost is turned to provide adequate aeration contain much of the nutrient values in the decomposing organic materials. The resulting compost is a more-or-less inert humus with few if any beneficial constituents. Other potential values are lost to leachates formed and washed away during the composting process.

Agricultural spraying of livestock wastes is an example of another traditional biowaste salvage process. Though thought to be beneficial, this process actually increases pollution while reducing nutritional values potentially available from the biowaste. Typically, dairy wastes from clean-up and wash down of milking barns are collected in a pond or lagoon. The biowastes are loaded with valuable, biologically active microorganisms, enzymes and other digestive factors and partially digested or unspent nutrients which decompose as they are held in the containment area. Depending on conditions at this site, a multitude of noxious and toxic offgases and liquids are generated. Economically important materials are taken off in these offgases and exudates. These include values most needed as plant nutrients—nitrogen and sulfur.

Subsequent high pressure spraying forces stored gases out of the mixture, releasing the remaining values into the air as pollutants. The depleted waste reaching the soil and vegetation has little, if any, value. These immense losses to the soil and flora must be made up for with synthetic fertilizers and nutrients, representing a staggering and completely avoidable economic loss. Agricultural spraying of livestock wastes is also very wasteful of water. The concentration of water to solids in residues generated by washing down stalls, barns and the like is on the order of 95% water to 5% solids.

Current additives such as "polymers" (proprietary agglomerates) to the washdown water are not the answer. Additives used to enhance the concentration, compaction by dewatering, and separation of water borne animal wastes as well as waste waters from other industries either result in poor quality separations or alterations in the character of many waste constituents from potentially useable to toxic.

In short, there is currently lacking any technique or products for so treating biowastes as to: immobilize, neutralize or prevent the formation of noxious, toxic and even explosive volatiles and leachates; to more effectively compact biowastes and thereby make more effective use of waste processing systems and sites; to improve retention and recovery of potential economic values; to provide practical methods of insect, pest and disease vector control; to recover significant inherent values in the form of improved, traditional or new products or to improve pollution control in the collecting, treating, transporting and disposing of biowastes.

SUMMARY AND GENERAL DESCRIPTION OF THE INVENTION

There have now been invented and disclosed herein certain new and novel methods and materials for stabilizing biological wastes which are free of the above-discussed disadvantages of processes and products heretofore available for that purpose.

Speaking generally, the biowaste stabilization techniques disclosed herein entail the application of a polyfunctional biowaste treatment complex (PBTC) to a biowaste: to replace conventional surfactants in a manner also providing biowaste stabilization, retarded pollutants; to neutralize offensive substances released from the biowaste in the form of exudates and VC's and other noisome offgases; to inhibit the release of such substances by sequestration, complexing and other mechanisms; to sequester and thereby conserve inherent materials of value; to augment the potential value of biowaste components; to shorten biowaste treatment times; to reduce noxiousness of present waste handling, transportation and processing systems permitting them to operate more effectively and safely with only minimal alterations; to better worker conditions; to reduce attractancy thus providing improved pest and disease vector control; and to facilitate the dewatering and concentration of biowastes and thereby conserve the space available in scarce and expensive waste disposal sites.

The principal or primary constituents of a PBTC are all polyfunctional. These constituents are:

a surface active treatment agent/synergizer (TA/S), an oligodynamic metal source (OMS), and a synergizable, biowaste stabilizing and vapor neutralizing reactant/photosensitizer (SR/P).

The foregoing primary constituent designators identify what will commonly be the most important functions of those constituents. This approach has been adopted for the sake of brevity and conciseness but is not intended to imply that those stated are the only capabilities which the primary constituents have. Other, at times even equally important functions of these primary constituents will be discussed below.

A PBTC in its simplest form is a synergistic combination of surfactant, metal and aldehyde components. A simple PBTC therefore superficially resembles a metal soap. The differences in characteristics and function, however, are vastly different. The high degree of biowaste interaction of PBTC's can not under any circumstances be anticipated from a knowledge of the functionality and characteristics of metal soaps which are in actuality entirely unrelated in any respect whatsoever.

The TA/S constituent is comprised of at least one of the class of surfactants, surfactant precursors and solvents. The OMS can be provided in elemental or combined form. In many cases, a metallohalogen compound will prove the most advantageous. The SR/P is typically an aldehyde although other compounds with the requisite functions are available and can be employed instead.

Once their assigned preliminary functions have been performed, one or more of these PBTC components in reacted or surplus form may perform additional functions and thereby provide added benefits—for example, by governing the release of complexed nutrients which, if released too quickly or easily from the improved or stabilized biowaste, might otherwise yield unwanted pollution or damage and detract from a valuable end use of the processed biowaste.

The selection of components for a particular PBTC is dependent upon the biowaste to be treated and the specific objectives of the treatment.

An initial consideration in TA/S selection is compatibility with a given biowaste substrate. Another requisite is that the TA/S must provide and/or facilitate such necessary functions of the PBTC as: good PBTC/substrate contact, detergency, solvency, sorbency, wetting, diffusion, vapor-to-vapor reactions, protein and lipid ineractions, dewatering, conservation of potential values, improvement in end product values, compaction and the many other possible facilitating functions which make efficient neutralization and stabilization of biowastes possible.

A second primary consideration in the selection of a TA/S is its ability to maximize the effectiveness of the biowaste treatment complex. The next consideration is the maximization of value retention and improvement of biowaste in materials produced by interaction of the PBTC with, and the addition of that complex to, the PBTC. Finally, selection of a TA/S should be related to maximum stability of the biowaste in terms of yielding treated products of reduced toxicity and noxiousness.

Anionic, cationic, non-ionic and amphoteric (zwitterionic) surfactants and judicious combinations of such surfactants may all be employed, depending upon such factors as the characteristics of the biowaste being treated, the application-specific objectives of the treatment and the ultimate destiny of the treatment complex or system. To provide maximum synergism with other components of the system, the surfactant may be chosen to provide a high degree of reactivity and provided in excess to the biowaste substrate so that, throughout the biowaste stabilization process, the TA/S will be a primary reactant and still provide facilitating concentrations for other PBTC component/substrate interactions.

The oligodynamic metal—aluminum, copper, zirconium, zinc, magnesium, manganese, silver or iron—is chosen for its ability to interact in many roles with a wide range of materials in the biowaste. The metal may act, for example, as a catalyst, a Lewis acid, a Bransted acid, an ion acceptor, an adduct former, a ligand, a cross-linking agent or an electrophile and, in some cases, as a biosterilant, as part of a protein product inclusion complex or a sorbent. In most PBTC applications, such as the treatment of carboxylic acid components of sewage for example, it is preferred that the metal or metallohalide source be one which provides a strong electrolyte in the treatment of the biowaste.

In this respect, the OMS may also be chosen for its ability to synergistically cooperate with the TA/S in the biowaste treatment process. For example, where the substrate is high in N or S, high in water, low in solids and of high pH, the combination of a cationic, pH buffering TA/S and a metal such as reduced copper results in a plurality of immediate interactions which cause dramatic neutralization and stabilization of the substrate.

The anionic or donor capability and cationic or acceptor capability of the TA/S may be used up in forming coordination complexes in conjunction with the oligodynamic metal source constituents, leaving that TA/S unable to perform such important synergistic functions such as dispersion, detergency, solvency, sorbency and wetting of substrate ligands. To insure against this possibility, one or more additional surfactants of non-ionic and even amphoteric character can be added to the complex.

The addition of a second, system compatible surfactant to a PBTC may thus dramatically improve interactions between the PBTC and a biowaste by eliminating or reducing incompatabilities which interfere with these interactions. This is also true for volatiles evolved from biowaste substrates if one or more of the PBTC components are vapor-to-vapor interactive or provide a sorbing or condensing mechanism to trap evolved volatiles and provide more intimate contact and additional reaction time. The PBTC may act at the substrate interface to intercept volatiles and to arrest or retard the formation of volatiles. These reactions may simply stop breakdown interference by: cross-linking protein and protein breakdown products, minimizing or eliminating enzyme poisoning breakdown mechanisms or producing more durable complexes which interrupt the ongoing anabolic cycle.

In applications involving biowaste substrates containing protein and protein breakdown products such as peptides and amines, copper is often the preferred oligodynamic metal. Copper demonstrates a remarkable ability to form a bond at pH 7 to peptide nitrogen. Cu (and Fe) also simultaneously and indiscriminately catalyze both oxidation and hydrolysis. In its elemental form copper is the best selection for the broadest application. However, while it may interact with a broad variety of biowaste substrates, the products of the interaction are of only moderate stability. To assure a greater range of action and degree of stability, cupric copper (or aluminum or ferric iron) and the like may be employed.

Also, if a wider degree of interactancy by such mechanisms as catalysis, coordination compounding, floccing, precipitation, compacting and the like between the PBTC system and biowaste solids is desirable, additional oligodynamic metals such as aluminum, silver, zinc, magnesium, manganese, zirconium and iron or sources of these metals may be added. Such additions can result in increased aggregation of solids and dramatic reductions in volatile emissions as well as such additional functions as agglomeration, hydrolysis and dewatering.

Nickel and cobalt, while oligodynamically active in biowaste treatment, are of very limited use due to toxicological and cost considerations. They also tend to be relatively ineffective except when applied under exceptional anaerobic conditions where nickel may compete very effectively with copper.

Calcium compounds such as calcium chloride and carbonate exhibit no oligodynamic properties of consequence. However, they may often advantageously be used as "sweetener" and in the humectant conditioning of biowastes.

The third primary PBTC constituent—the SR/P—is selected for its biowaste stabilization capabilities and its ability to neutralize VC's by vapor phase reactions. In many cases, this constituent is also selected for its ability to sensitize and promote the activity of the complex by ultraviolet radiation in a manner which makes the complex significantly more effective—in a typical case by an order of magnitude or more.

Photosensitized activity of a character useful in biowaste treatment is exhibited by even the simplest, two component PBTC's such as those comprised of silver and AEPD (3-amino-2-ethyl-1,3-propanediol). In this simplest case the silver apparently endows the complex with the appropriate degree of interactancy/photosensitivity; and the overall PBTC system not only provides rapid and more effective PBTC/biowaste interactions such as neutralization of VC's and increased effectiveness in terms of reactivity with the biomass but, upon exposure to light, provides a definitive partitioning of biomass solids and aqueous liquids by phase separation. This phenomenon is not well understood, and it is possible that the AEPD enhances the photosensitivity of the silver just as benzaldehyde, benzil or benzoic acid does in the presence of copper and other metal ions. In any event, the photosensitivity enhances biomass treatments by mechanisms including more effective stabilization of biomass components; provides quicker and more effective solid/liquid separations in the presence of ambient light and quicker, more effective vapor reductions requiring less PBTC and making marginally effective combinations with silver and other OMS ions considerably more effective than otherwise.

In some instances the metal contributes to photosensitivity but in others it merely has activity enhanced by a photosensitizing aid which makes the complex more effective. The effectiveness of photosensitive PBTC complexes against biomass waste components may be a result of photolysis (photochemical decomposition), photo induced polymerization, oxidation and ionizations and fluorescence and phosphorescence. Free radicals are probably involved, these acting as initiators or intermediates in oxidation, photolysis and polymerization.

SR/P compounds which are known to contribute to enhanced oligodynamic effectiveness or in conjunction with other constituents make PBTC's more effective include aldehydes such as benzaldehyde, aldehyde mixtures, benzoic acid, benzil, and benzoyl peroxide. The SR/P also participates in combination with other PBTC components in interactions including oxidation, reduction, addition, polymerization, destruction of living organisms, odor recharacterization and vapor-to-vapor interactions with volatile and nonvolatile constituents of biowastes. A major advantage of the SR/P component is its ability in conjunction with other components to prevent formation of, neutralize or otherwise make less harmful the interstitial and fugitive volatiles emitted from biowaste.

As suggested in the foregoing discussion of photosensitized PBTC's, it is possible by judicious selection from the three types of primary components discussed above to provide a two-component PBTC system with the ability to effectively treat many biowaste substrates such as some leachates and sludges. In this case, because silver has both oligodynamic and photosensitive characteristics, two primary PBTC requirements in addition to SR/P functions are provided by the second constituent of the two-component system—an SR/P such AEPD. As mentioned previously, the favorable biomass waste treating capacity of the two component system is believed to result primarily from forces related to endowment of the system with an appropriate degree of photosensitivity, however obtained. Effectiveness of the few known examples of two component PBTC's is nevertheless enhanced or improved by addition of a TA/S.

More typical, however, and effective for more difficult biowaste treatments, is the synergistic combination of the three primary PBTC constituents—a TA/S, TA/S precursor or source; an OMS which may often advantageously be a metallohalogen compound or a complex which is a source of a type a or type b Lewis acid and a SR/P with photosensitization capabilities.

There are biowastes which include stable forms of noxious and toxic matter, usually the original matter comprising some or most of a given biowaste. Such stable materials include complex saturated and unsaturated hydrocarbons of biological origin or resulting from commingling of wastes such as aromatic and paraffinic hydrocarbons and heterocyclic compounds and the like including natural resins, tars, petroleum, and solvents such as benzenes, toluenes, terpenes, terpenoids and the like. When these more treatment resistant classes of substrates are encountered in a biowaste, the addition of a fourth class of component—a metallohalogen augmenter of the OMS or other halogen source—provides more complete stabilization of the biowaste.

Thus, both three and four component systems may advantageously include a halogen source—a halide of an oligodynamic metal in the case of a three component system and a halogen augmenter which may or may not include an oligodynamic metal if a four component complex is selected although a metallohalogen augmenter containing an oligodynamic metal is preferred.

There are instances where a particular biowaste is high in bound copper, and it may be impractical to provide a PBTC component to reactivate that copper as an "active" constituent of PBTC and consequently inappropriate to use more copper as an oligodynamic component. Aluminum, iron, zirconium, silver and particularly zinc, alone or in combination, can be substituted in this capacity. However, it will frequently require at least two metals to replace copper in the treatment of most biowastes. Aluminum and iron, aluminum and zinc, aluminum and silver, and silver plus zinc or iron are all usable combinations. Another instance, requiring copper plus another metal, is where copper has been or is likely to be consumed in the treatment process; and there is no excess.

In many applications of the invention, decomposition of a biowaste will have proceeded to a degree where emissions of volatiles are already substantial; and supplemental concentrations in the PBTC of remedial vapor-to-vapor reactants are required in compensatory response. In other cases, only inherent emission sources in the biowaste need to be treated. There, the SR/P may be supplemented to assist in vapor-to-vapor neutralization of interstitially stored volatiles, but the SR/P is an important constituent and needs to: (1) be available and participate in forming synergistic complexes of the OMS and to interact with the OMS and complexes formed therefrom in polymerizing and cross-linking proteinaceous and other constituents of biowaste substrates; (2) interact in the vapor phase with biowaste volatiles; and (3) provide some odor recharacterization to the biowaste substrate. It is preferable in these circumstances to provide a PBTC with fifth primary ingredient—a volatile acid or ammonium ion source which reinforces vapor-to-vapor interactions, interdiction or restraint against the emission of noxious and toxic volatiles. The volatile acid, ammonium ion source or complexes thereof may also be used in lieu of the halogen ion source if the latter is not necessary for treating anomalous components in a particular biowaste. There will be occasions, however, where both a halogen and a volatile acid, an ammonium ion source may be required.

Almost any compatible volatile acid or volatile acid complex or ammoniacal ion source may be used. The preferred volatile acids are hydrochloric and acetic, the preferred complexes are surfactants based on those or sulfuric acid salts, and the preferred ammonium ion source is ammonium hydroxide (or aqua ammonia). The ammoniacal ion can alternatively be provided by a TA/S such as benzalkonium chloride or an ammonium salt-containing surfactant. An alternative to the acid is a surfactant based on said acid salt.

In systems with two, three, four and even five primary components, the PBTC constituents all operate synergistically; and the PBTC unexpectedly and uncharacteristically functions, when interacted with biowastes, as if it contained a much larger number and concentration of separate constituents including:

|  | Volatiles | Solids | Liquids |
| --- | --- | --- | --- |
| a wetting agent, | ✓ | ✓ | ✓ |
| a sequebtrant, |  | ✓ | ✓ |
| a cleaning agent, | ✓ | ✓ | ✓ |
| a penetration aid, | ✓ | ✓ | ✓ |

-continued

|  | Volatiles | Solids | Liquids |
|---|---|---|---|
| a dispersant, | ✓ |  | ✓ |
| an ionic antagonist, | ✓ |  | ✓ |
| an odor characterizer and/or recharacterizer, | ✓ | ✓ | ✓ |
| a polar reaction component, | ✓ |  | ✓ |
| a nitrogen, sulfur binder/ligand acceptor, donor, | ✓ | ✓ | ✓ |
| a carboxylic acid (COOH) binder, | ✓ | ✓ | ✓ |
| a protein and protein breakdown product complexing and fixing agent, | ✓ | ✓ | ✓ |
| a reducing agent, | ✓ | ✓ | ✓ |
| a polymerizing and cross-linking agent/OMS aid, |  | ✓ |  |
| a biowaste neutralization promoting catalyst, | ✓ | ✓ | ✓ |
| a nitrogen fixative, | ✓ | ✓ | ✓ |
| a sulfur fixative, | ✓ | ✓ | ✓ |
| a fatty acid reactant, | ✓ | ✓ | ✓ |
| a dewatering agent, | ✓ | ✓ | ✓ |
| a compaction aid, |  | ✓ | ✓ |
| a precipitation aid, | ✓ |  | ✓ |
| a floccing aid, |  |  | ✓ |
| an aggregation aid, |  |  | ✓ |
| a buffer, | ✓ | ✓ | ✓ |
| a sorption aid, | ✓ |  |  |
| a solubilization aid, | ✓ |  | ✓ |
| a micronutrient/ | ✓ | ✓ | ✓ |
| a vapor-to-liquid, vapor-to-solid and vapor-to-vapor reactant, | ✓ | ✓ | ✓ |
| a hydrocarbon reactant, | ✓ | ✓ | ✓ |
| a terpene or sesquiterpene reactant. | ✓ | ✓ | ✓ |

Other, secondary constituents can often be advantageously incorporated in a PBTC or derived from the PBTC in the course of the biowaste treatment. A by no means exhaustive list of useful secondary constituents includes:

a humectant, an odor characterizing agent, an odor recharacterizing agent, an antioxidant, an insect and/or animal repellent, a scavenger, a fermentation or other digestive microorganism, an oxygen source, a sterilant, a biocide, a biostat, a chelate, a clathrate (inclusion compound), an enzyme and/or other catalyst, an indicator dye, a marking dye, a gelling agent, a foaming agent, a soil amendment, a barrier layer former, a cellulosic interactant cover or containment film former, elements for effecting a controlled release of selected components from the PBTC.

Any product requiring separate components for the above-identified distinct functions of the primary constituents in a PBTC or even near this many primary ingredients, let alone one with optional constituents, would be impractical. One very important advantage of the novel PBTC systems disclosed herein is that they typically have only few components, yet can have at a minimum all of the primary functions (and additional optional functions) identified above when applied to complex biowaste systems such as organic sludges, hospital wastes, landfills, fish and meat processing wastes, poultry and poultry wastes, mushroom bedding and leachates or many less complex systems such as composts, livestock fecal wastes, sewage, food processing and other biowaste lagoons and the like. Although only a very few components are absolutely essential, the actual number of constituents in a PBTC designed for a particular specific application may vary, depending upon such parameters as the nature of the biowaste being treated, the manner in which the PBTC is to be applied, and the objective of the treatment in a particular application.

The composition of a PBTC appropriate for the treatment of a given biowaste may be determined by: analysis of the basic substrate to be treated, review of process parameters, determination of the desired effects and identification of end products which may be retained or made available to improve biowaste value and to stabilize and prevent pollution by biowaste substrates.

A typically less complicated approach, and one which produces more than satisfactory results in most instances, is to base the composition of the PBTC on the ionic character of the dominant species in the offgas from the biowaste being treated. While the offgases vary considerably from one biowaste substrate to another, there is usually a dominant polar/ionic species except in very rare instances. The polar/ionic (ligand/acceptor) nature of dominant offgas components offers considerable useful information about the chemical nature of the biowaste substrate from which it is derived and also provides a good indicator of where the substrate is in the anabolic process of substrate decomposition.

In a few instances such as those involving the treatment of biowastes where petroleum products, solvents or terpenes, olefins and similar hydrocarbons may be present, the offgases may exhibit little or no polar charge. In others cases such as more mature landfills, offgases from deeper layers may be of a more substantially intermixed ionic character. In these cases, also, information on the nature of the offgas can lead directly to the formulation of a PBTC for effectively treating the biowaste giving off the gas(es).

In most cases, formulation of the PBTC to neutralize the biowaste offgases based on the polar/ionic nature of these gases is also required or at least advantageous. Usually, the offgases will include very weakly polar or non-ionic volatiles which may also require treatment.

Most complex forms of biowaste such as food processing wastes are in liquid form or of a more solid form such as municipal garbage which emit leachates and gases comprised of such chemical species as primary, secondary and tertiary amines; ammonia; carboxylic acids; sulfides; thio compounds and the like. Resins, solvents, and olefins and other hydrocarbons are with certain notable exceptions seldom consistently present to any substantial degree.

A less complex biowaste than many of those alluded to above is compost. This biowaste is usually all plant matter—leaves, branches, twigs, grass trimmings, vegetable and fruit peels, sewage, etc. Decomposition of compost frequently yields condensates, liquids and offgases in which hydrocarbons—particularly terpenes, phenolics and other compounds with complex ring structures—coexist with protein and lipid breakdown products. Treatment of composts with a PBTC as described herein is particularly effective and yields a more useful fodder, fertilizer, fermentation stock or humus due to the retention of valuable nutrients which are retained as a result of PBTC treatment and are not lost as fugitive volatile pollutants.

Whether organic or inorganic, the vast majority of compositions in the biomass substrate and present as gases evolved therefrom are characterized by one of five basic moieties—N (nitrogen), S (sulfur), COOH (carboxylic), $C_2h_2$ (resins/solvents) and heterocyclics. Of these, N and S will with certain exceptions be present in the majority and COOH and $C_2H_2$ present in the minority of the substrate materials which cause pollution and/or have valuable end product potential. In short, the principal sources of pollution in most biowastes are those constituents containing sulfur and nitrogen with fatty acids and their derivatives also commonly being present. These ubiquitous biowaste macroconstituents manifest themselves in a wide variety of anabolic byproducts and may occur in gas, liquid and solid states.

Where possible, the PBTC is formulated to so treat and complement a given biowaste as to provide a substrate for selected fermentation organisms. In this way, the biowaste may be constructively altered to enhance processing of the biowaste and/or to provide valuable fermentation products and byproducts which may enhance the value of the biowaste, or increase by conversion of otherwise noxious components, valuable, recoverable end products or byproducts.

The principal sulfur compounds found in waste waters are sulfates. The most common volatile sulfur compound responsible for atmospheric pollution are sulfur dioxides and hydrogen sulfide. Many offensive organic sulfur compounds such as the mercaptans are also found in biowastes.

Sulfur compounds are generally more difficult to treat when the sulfur is present in a heterocyclic ring. Both organic and inorganic volatile sulfur compounds are resistant to neutralization, immobilization and preservation by currently known biowaste treatments.

Neutralization and sequestration of sulfurous biowaste compounds resolves an important pollution problem and preserves a valuable resource which can be recycled in fertilizers, soil amendments, fodders, composts and such. The same is of course true for nitrates and other nitrogen compounds.

Nitrogen is a macro nutrient for vegetation and should at all opportunities in treating biowastes be conserved in a form that makes the nitrogen available as a potential nutrient rather than being released into liquid or air as a pollutant.

Nitrogen and sulfur based TP/S's are in this regard sometimes preferred for PBTC's as the spent or excess PBTC can then make a positive contribution to the raw material potential of the treated biowaste. For similar reasons, oligodynamic metals can be selected from those which may contribute important micronutrients to biowastes used as fermentation stocks, as composts or fertilizers. This may be particularly important in regions where biowastes may be used as fodders, high value fertilizers, soil amendments and value added or process-accelerating fermentation stocks or fermentation valuable products and byproducts.

Formulation of an appropriate, if not optimal, PBTC is made easier by virtue of the limited number of relationships that commonly exist among the different types of pollutants in biowaste offgases. A biowaste offgas high in nitrogenous compounds, for example, will typically contain few if any fatty acids although there may be some coexistent vapors with sulfur radicals. The converse is also true; biowastes high in fatty acids will typically emit relatively small amounts of nitrogenous compounds and few if any sulfur based volatiles.

Nitrogenous offgases usually indicate that proteins or proteinaceous compounds dominate the biowaste substrate (the presence of volatiles with sulfur radicals may also indicate the presence of sulfur bearing proteins but can arise as a result of other factors). If lipids are present, their breakdown will be suppressed or sequestered by the greater concentrations of nitrogen and sulfur resulting from anabolic decomposition. Conversely, when fatty or other carboxylic acids are in the majority, they dominate some, if not all, of the nitrogenous and sulfur volatiles of a substrate.

Carbohydrates usually become carbon sources for microorganisms. Depending on the process conditions in the substrate—aerobic or anaerobic—, available micronutrients, substrate pH, available oxygen and other parameters, one or more dominant species will be favored. The resulting polar/ionic nature of offgases is related to characteristics common to decomposition and microbial products formed during biowaste processing and as a result of treatment.

Metabolites and inherent components of the biowaste make up the chemical species requiring treatment. These include proteins, peptides, polypeptides, amines, fermentation products and byproducts, esters, phenols, ethers, alcohols, organic acids, glycols, terpenes, sesquiterpenes and the like. Conditioners, macro and micronutrients, catalysts and even innoculums and other PBTC ingredients can be utilized to favor one microbial species and the consequent production of beneficial metabolites. Moreover, the fundamental character of the biowaste itself may be altered and process efficiency improved at the same time.

Decomposition products comprised of aromatic and unsaturated olefins—terpenes, sesquiterpenes and particular species such as limonene, pinene and campbenes, for example, are the most resistant to treatment. However, modification of the basic PBTC formulation with a halogen, usually in conjunction with an oligodynamic cation, will, with the aid of solventizing and sorptive action over time, readily complex or otherwise sequester these difficult-to-treat volatile organic compounds. Also, where terpenes are encountered, the addition of specific solubilizers such as propylene glycol and glacial acetic acid may facilitate sorption and reactions. For this reason, solubilizers for the foregoing organic compositions are usually incorporated into the PBTC. As a result, desirable reactions which might not otherwise occur may take place over time once volatiles have been sequestered or otherwise acted upon.

Normally, undecomposed biowastes exhibit significantly higher raw material potential if preserved early in anabolysis and are a substantial cause of noxious and toxic pollution if they are not.

Also, in those instances where greater stability of the biowaste is desired, solubilizers may be employed to further enhance interaction between the PBTC and the biowaste. This is particularly true if biowaste processing is to be improved and if there is a potential end use for the biowaste.

Biowastes high in lipids usually produce pollutants dominated by liquids and offgases containing carboxylic acids and esters. In such instances, a PBTC containing at least one TA/S of the antagonistic ionic type may be used but a PBTC containing one or more cationic, nonionic and/or amphoteric compositions is preferred. The surface active composition is polyfunctionally used in this case as a polar VC antagonist to control polar dominated biowaste breakdown products. While there will normally be enough polar antagonistic surfactant to perform the required functions, it is sometimes practical to include an additional, PBTC/biowaste compatible surfactant. This ensures that, if all of the antagonistic surfactant is reacted, sufficient synergistic benefits of the reserve or secondary surfactant are available to wet the biowaste surface, promote penetration and provide other interactions necessary to achieve treatment objectives consistent with various biowaste substrates.

PBTC treatment complexes may be structured from a practical viewpoint in five basic formula types. In representative cases water is the carrier.

The first basic class of PBTC's is a two-component system or complex. It has an oligodynamic metal or source and a vapor neutralizing reactant/photosensitizer but no treatment agent/synergizer. However, even the most broadly effective two-component PBTC is profoundly improved in function when an appropriate TA/S is included.

As a general rule, a PBTC with only these two of the three primary constituents described above will not function well against that portion of a biowaste substrate which is high in carboxylic acids or hydrocarbons unless it contains a halogen, preferably in metallohalogen form. For treating volatile biowaste hydrocarbons and carboxylic compounds, aluminum is the preferred metal and bromine the preferred halogen.

A useful optional component of a two-primary constituent (or other) PBTC in applications where carboxylic acids are not present can strangely enough be a carboxylic acid or carboxylic surfactant compound. A good example is where decomposition of the biowaste has proceeded so far that a major portion of its nitrogen is in the form of ammonia and amines. Addition of a TA/S selected from those containing volatile carboxylic acids or volatile carboxylic acid surfactants added per se to the PBTC may provide a very efficient mechanism for forming a salt which may be reincorporated or retained in the substrate in a form conserving later potential use of values the biowaste substrate.

The just discussed option is not limited to use of a carboxylic acid. Any electron acceptor comparable in volatility to the nitrogen compound may be used.

The second PBTC form, comprised of all three primary components, may or may not contain a halogen although it is usually preferred that a halogen be present. This requirement, and the one for an OMS, can be satisfied by providing both the halogen and the OMS together or in a metallohalogen complex.

Most preferred halogen complex metals are aluminum, copper, zinc, magnesium, silver, manganese, zirconium, titanium and iron. The preferred halides are chlorine and bromine. The preferred SR/P synergists for PBTC's with metallohalogen complexes are benzil, benzoin, benzoyl peroxide, benzoic acid and benzaldehyde. In the case of PBTC's utilized for treating biowastes with significant hydrocarbon contents (particularly aromatic hydrocarbons), the preferred combinations of OMS and SR/P in order are:

Aluminum: Benzoin, benzaldehyde.

Copper: Benzoin, benzil, benzaldehyde, benzoic acid, benzoyl peroxide.

Zirconium: Benzaldehyde, benzoic acid.

Zinc: Benzoin, benzaldehyde.

Magnesium: Benzoic acid, benzil.

Titanium: Benzaldehyde, glyoxal.

Manganese: Benzoin, benzaldehyde, benzoic acid.

Iron: Benzaldehyde, benzoic acid.

Silver: Benzoic acid, benzaldehyde.

When combined to form polyfunctional synergists of other or mixed oligodynamic metals, a SR/P in the following order of preference is employed: benzaldehyde, benzoic acid, benzil, benzoyl peroxide.

The synergistic complexes formed by combining the primary constituents in a PBTC tend to be more or less light sensitive under appropriate circumstances and may be activated for the most efficient treatment of biowaste substrates with light. Unfiltered natural light is preferred but other types of light, such as fluorescent and incandescent, can be employed when the use of natural light is not possible or convenient. When artificial, light in or about the near ultraviolet such as that emitted from a conventional 2357 angstrom source is preferred.

It was pointed out above that sulfur is an important plant microbial and animal nutrient and should at all opportunities in treating biowastes be conserved for its nutrient value rather than being released from the biowaste as a pollutant. Sulfur bearing TA/S's are sometimes preferred, especially for PBTC's which, spent or residual, have nutritional potential in treated biowastes used as fodders, soil amendments, fermentation substrates, fermentation products or fertilizers. For similar reasons, when TA/S's with a basic pH such are used, potassium salts are preferred over sodium.

PBTC's may be added directly to biowastes wherever and however they occur. They may be diluted with fluid carriers including air, water and organic solvents and sprayed over or into heaps, windrows or piles. They may be used in concentrated but usually diluted form for scrubbing or otherwise treating biowaste-containing process and other effluents. They may be added to fluid streams containing biowaste products. They may be mixed and injected into and onto biowaste substrates. They may be made into pastes or gels and placed near, upon, or in biowaste wastes or in water to form a biowaste-treating liquid. The PBTC may be incorporated into a foam or fiber matrix employed in forming a protective and interactive barrier on or in biowaste substrates. Such foams or foam and cellulosic fiber composites may be used as blankets and packing for both liquid and solid biowastes wjen liquids or volatiles may be contacted. PBTC's may also be employed as treatment complexes in covers made of waste paper or other suitable matrices which may be applied as biowaste interactive laminars, films or barriers to cover, contain, incorporate, contact and layer biowastes.

PBTC's can be also sprayed onto the surface of a biowaste holding pond or lagoon. They can be added to toilet water and mixed with the wash or rinse water employed to clean receptacles and transportation and handling equipment such as pipelines, trucks, augers, bulldozers, loaders and the like. Many other techniques for applying liquid PBTC's can also be employed. Essentially, the only restriction is that the technique selected be one which results in intimate contact between the complex and the biowaste substrates requiring treatment.

Depending on the particular biowaste waste application, improvements and controls obtained by treating a biowaste with a PBTC as described herein may include: improved removal of biowastes from surfaces; reduction in decompositional liquefaction and offgasing of noxious and toxic substances; reduction of processing time; homogeneity of process and end products; the ability to direct reactions along optimal lines; improved space utilization by compaction; sequestration and complexing of valuable components otherwise lost by liquefaction and offgasing; reduction in the toxicity of leachates and other liquid waste effluents; vapor-to-vapor and contact interaction with liquids and fugitive volatiles which may be captured and retained in the substrate; reduction in air pollution emissions at all points of biowaste handling and processing; reductions in substrate odors; scavenger, pest, vermin and insect control; improved worker safety; improved economy and effectiveness of process controls and applications; neutralization or retardation of anabolic processes which might produce noxious and toxic metabolites; the facilitation of biowaste treatment by aggregation of the solids in liquid biowaste wastes; containment of offensive vapors and exudates; improved public relations; and the availability of new or considerably improved end products.

A number of the objects, features and advantages of the present invention have been identified above. Other important objects, features and advantages will be apparent to the reader from the foregoing, the appended claims and the ensuing entailed description and discussion of the invention.

DETAILED DESCRIPTION OF THE INVENTION

The polyfunctional biowaste treatment complexes of the present invention are applied to organic wastes to, at a minimum: stabilize the biowaste, inactivate components of the biowaste which are noxious or toxic or which have degradation products of that character and neutralize offensive vapors and exudates during the stabilization and component inactivation process. These novel complexes are so formulated that they have at least the following functions:

- wetting, diffusion and penetration of the biowaste by the components of the complex;
- vapor-to-vapor neutralization of malodors released from the biowaste;
- inactivation and/or immobilization of noxious and toxic biowaste components; and
- promotion of reactions which convert noxious and toxic biowaste components to less or totally harmless substances or substances with economic potential.

These and other significant functions can be obtained by formulating the complex to include the following functionalities:

| Range | Preferred (Percent) |
|---|---|
| Ionic reactant/wetting agent/ penetration, dispersion, contacting, solubilizing, and reaction aid | 1 to 80 |
| Nonionic, amphoteric wetting/penetrating/ contacting/solubilizing/reaction and dispersing aid | 1 to 80 |
| Protein/polypeptide protein breakdown product/deamination and hydrolyzation reaction aid | 1 to 50 |
| Vapor-to-vapor and contact protein breakdown product/complexing, cross-linking, polymerizing, synergising and reaction aid | 1 to 50 |
| Oligodynamic metal/metal complex, ligand acceptor/compacting, floccing, complexing, and cross-linking aid/micronutrient | 1 to 80 |
| Sulfur radical trapping and reaction aid | 1 to 50 |
| Nitrogen radical trapping and reaction aid | 1 to 70 |
| Hydrocarbon solubilizing and reaction aid | 1 to 50 |
| Sorbing aid | 1 to 80 |
| Non-polluting odor recharacterizer | 0 to 10 |
| Buffer | 1 to 50 |
| Vapor-to-vapor reactant/ volatile acid vapor neutralizer | 1 to 50 |

The PBTC can be provided in concentrated form and diluted before use. Functionalities in diluted PBTC's will typically be present in concentrations falling in the foregoing ranges.

As pointed out above and discussed in more detail below, some of these tabulated reactant/reactant promoters may be marginally a synergistic combination of as few as two constituents—for example, the OMS, SR/P combination of primary constituents used to treat leachates.

More commonly, however, most biowaste systems require all or most of the tabulated functionalities provided by employing synergistic combinations of at least one of each of three types of PBTC constituents or a source of each such constituent—a TA/S, an OMS, and a SR/P which is usually an aldehyde or source thereof.

In other polyfunctional complexes which can be employed to treat a great variety of unrelated biowastes, all or almost all of the tabulated reactants/reactant promoters are supplied by a synergistic combination of four PBTC constituents or their sources—the same constituents employed in a three-component complex plus a halogen source.

In treating biowaste or constituents thereof which are primarily non-ionic, compatible additives such as benzoic acid may be added to the foregoing PBTC's to promote favorable actions with hydrocarbons and comparable compounds with pollution potential.

An alternative for treating biowastes already in advanced stages of decomposition is to add a volatile acid source to the PBTC for increased vapor-to-vapor interaction. The halogen is included if the biowaste contains hydrocarbons which can be effectively treated if the volatile acid is present.

In all of these PBTC's, the TA/S, typically a surfactant, is employed as a conditioner, wetting, penetration, solvent, sorption, dispersion and reaction facilitation agent and for the ability of appropriate ligand or ion acceptor type surfactants to synergistically react with and participate in the neutralization of noxious and toxic compounds found in and about biowastes.

Anionic, cationic, nonionic and amphoteric surfactants are all useful with the selection of a particular surfactant being based on such factors as the nature of the biowaste to be treated, cost, ease of formulation, etc. Particular types of surfactants that can be used include: soaps (sodium and potassium salts of fatty acids); rosin oils and tall oil; alkylarenesulfonates; alkyl sulfates; straight chain hydrophobes; hydrophobes with primary and secondary branched groups; long chain acid esters of polyethylene glycol; polyethylene glycol ethers of alkyl phenols; polyethylene glycol ethers of long chain alcohols and mercaptans; fatty acid diethanolimides; block polymers of ethylene oxide and propylene oxide; quaternary ammonium compounds; carboxylates; aminocarboxylates; acylated protein hydrolysates; sulfonates; lignosulfonates; alkylbenzosulfonates; petroleum sulfonates; dialkylsulfosuccinates; natural sulfated oils; phosphate esters; polyoxyethylenes; ethoxylated alkylphenols; ethoxylated aliphatic alcohols; carboxylic esters; alkalies; phosphates; silicates; neutral double salts; and acids and, in some cases, insoluble inorganic builders such as bentonite, borax and bauxite which are hydrophilic colloids, emulsion stabilizers, suspending agents, sorbents, carriers and sources of oligodynamic metals and metals complexes. Ethanol, p-dioxane, carboxylic acids such as acetic acid and glycols such as polyethylene glycol may be used as supplemental or secondary surfactants where the biowaste includes aromatic or other hydrocarbons.

Properly selected surfactants promote synergistic interaction of other PBTC constituents among themselves and with the surfactant when the complex is applied to a biowaste.

They may also be selected to synergize and participate in reactions of constituents specific to some but not all biowastes such as the halogens and vapor-to-vapor interaction promoters discussed above.

Advantages of synergizing the constituents of a PBTC with a surfactant of the character just described include: reduction of reaction time; improved homogeneity of biowaste treatment processes and end products employing values preserved by those processes; more complete and efficient reactions and the direction of reactions along optimal lines; improved space utilization by effecting or promoting compaction of treated wastes; promotion of borderline reaction kinetics; promotion of fermentation process; facilitation and promotion of sequestration and complexing by other constituents of valuable components otherwise lost to offgasing; reductions in the toxicity of leachates and other liquid waste effluents; ion exchange neutralization of ionic biowaste substrates; dewatering of biowastes during or subsequent to treatment; reduction of air and water pollution; reductions in substrate odors; scavenger, pest, vermin and insect control; neutralization and retardation of anabolic processes; improved economics; usefulness for biowaste of widely divergent character; improved public relations; recovery of water useful for process and operational use and obtention of new or considerably improved end products from treated substrates.

The use of surfactants to form synergistic PBTC's with the myriad of capabilities described above contrasts markedly with the use heretofore made of surfactants in waste disposal. This has been limited to the above-discussed cleaning of collection/storage and transportation receptacles and other uses taking advantage of a surfactant's "cleaning" and limited bactericidal capabilities.

The second, and an equally important, constituent of a PBTC is a compatible oligodynamic metal, a source of such a metal, or a mixture of those metals or sources.

In the context of the present invention, oligodynamic metals are those which, as part of a synergistic PBTC, exhibit a profound interactive and generally neutralizing effect at very low concentrations on solid, liquid and volatile, noxious and toxic biowaste components. Among the compounds inactivated and neutralized by oligodynamic metals in PBTC's are proteins and protein degradation products including many polypeptides, amines and amino acids. Amines are among the most offensive of protein breakdown products from the viewpoint of their odor. Representative of the amines in this category are: methyl and triethylamines (strong fishy odor), indole and skatole (strong fecal odor) and cadaverine (dead body odor).

Also, associated with biowastes as original constituents are a wide variety of noxious and toxic sulfur compounds which can be effectively neutralized by the synergized oligodynamic metal constituent of the PBTC. Among these are compounds with SH groups or radicals such as hydrogen sulfide, ethanethiol ($C_2H_5SH$) and the like.

Other noisome substances effectively made harmless by the OMS constituent of a PBTC include: fatty and amino acids and their breakdown products and many petroleum and other hydrocarbons including those in resins, tars, solvents and derivatives such as benzene, toluene, pyridine, phenol and phenolic compounds, terpenes and terpenoids.

The selected oligodynamic metal performs a number of specific functions, any or all of which may come into play in a particular application of the invention. Acting synergistically with other PBTC constituents, this component of the complex may polymerize, catalyze, cross-link, serve as an ion acceptor or ligand and otherwise participate in helpful reactions which reduce and inactivate many biowaste constituents including volatile and non-volatile inorganic and organic compounds. In some important instances, it takes an active part in forming an organometallic bond between proteinaceous hydrocolloids which renders inoffensive many noxious and toxic biowaste components including anabolically generated intermediates which are precursors of offensive products. Also, the OMS constituent of a PBTC participates in or promotes a number of molecular bonding reactions including those involving Van der Waal's force and the formation of metallic, covalent, ionic, double, and bridge bonds—including those of the protonic and hydridic types—which stabilize and otherwise improve biowaste substrates and control pollution arising therefrom. These effects take place with respect to nitrogen, sulfur and carboxylic compounds and their products.

Copper, zinc, silver, iron, zirconium, magnesium, manganese and aluminum are all oligodynamically active.

Forms in which these and possibly other oligodynamic metal can be supplied include: colloids; halides and other mineral acid salts; carboxylic acid salts; oxides; other addition products; "activated" crude minerals such as baddeleyite, bauxite and alunite; "activated" slurries or liquids made from waste or recycled metals such as spent aluminum cans, copper wiring, zinc electrodes, scrap iron and waste photographic emulsions and varieties of colloidal quartz in which one or more oligodynamic metals are present as impurities. If the metals are chemically bound in a non-oligodynamic state, they must be treated to release cations and oligodynamically activate them. Depending on the metal, an acid or sometimes, as with aluminum, either an acid or base may be used for this purpose.

Of the polyvalent metals, copper—especially in its cuprous form—is preferred when the biowaste does not contain a very high concentration of mixed, nitrogenous and sulfurous radicals or significant proportions of carboxylic compositions. Copper chloride and sulfate are easy to handle, formulate and use; non-toxic at the levels at which they are used in PBTC's; biodegradable; widely available and inexpensive. In addition, copper is a micronutrient which many geographic areas and products are deficient in; and copper chloride and other copper compounds and complexes can remedy this deficiency. Copper sulfate has been approved for human and animal consumption and is widely used as a food supplement and processing aid. It is GRAS (generally regarded as safe), see 21CFR Ch. 1, §184.1261, §170.3(o)(20) and §170.3(o).

Indeed, copper sulfate is even used in infant formulations in accordance with sections 412(g) and 412(a)(2) of the Federal Food Drug and Cosmetics Act. Concentrations of this salt in infant formulations are usually greater than in PBTC's formulated in accord with the principles of the present invention.

The copper can also be supplied in other forms such as copper acetate, copper halide, copper bromate and copper gluconate with copper halides being preferred for many applications such as the treatment of agricultural livestock liquid wastes. Copper chloride is preferred for applications involving small concentrations of human body wastes, and copper bromide is preferred for some applications involving biowastes moderately high in carboxylic acids.

Despite the usual preference for copper, there are specific biowaste substrates which can be more efficiently treated with other oligodynamic metals and combinations of oligodynamic metals, particularly in the form of metallic complexes and metallohalides.

For example, aluminum exhibits the unusual property among the oligodynamic metals of being amphoteric; i.e., it has the capacity of behaving as an acid or a base. This property makes aluminum much more useful in a wider range of applications than can be justified strictly on its comparative oligodynamic performance. It can particularly benefit PBTC's intended for a wide range of biowastes of ionic nature. Aluminum is frequently employed as an adjunct to other oligodynamic metals to provide this benefit.

Aluminum is perhaps slightly better than copper for reducing carboxylic acids but only in combination with a halogen—preferably chlorine. Also, aluminum may be considerably more useful than copper in very wet systems where dewatering may be desirable since aluminum ions promote solids concentration by the formation of flocs as well as stabilization and neutralization of carboxyl-based biowaste substrates when employed in a halide form. The marked influencing of fatty acids, terpenes and the like carries over when the halide is a bromide rather than a chloride. Aluminum is most effective when accompanied by synergistic PBTC components that react with it and a halide to form metallohalide addition complexes; such components include benzaldehyde, benzoic acid and benzoin and solvents such as p-dioxane and ethanol. The beneficial effects of aluminum can be enhanced by exposing the biowaste to ultraviolet radiation—typically sunlight—in the course of the treatment.

Aluminum is also preferred as a sorbent for petroleum and other hydrocarbons. Its compounds catalyze hydrocarbons such as pinene into non-volatile resins. It is preferred (as a bromide) when cyclic hydrocarbons are encountered.

Copper and aluminum can be used in combination to treat a much wider range of harmful biowaste constituents than can be dealt with by either of these oligodynamic metals, used alone. In this synergistic combination of oligodynamic metals, copper provides the benefits of a "soft" Lewis acid and aluminum the benefits of a "hard" Lewis acid. The combination is all the more effective when a halogen is present, particularly in a compound of one or both metals.

All of the above-identified metals are effective against N and S radicals. Aluminum and zirconium are far more effective than the others in stabilizing and neutralizing carboxylic acids in biowaste substrates. While aluminum and to some extent iron promote floc formation in biowastes, silver and to a lesser extent copper are valuable for their ability to form precipitates. From another viewpoint, aluminum and iron are frequently preferred because both have very low toxicity and because they are usually cheaper than other metal sources. Despite current unsupported allusions in the popular press concerning a possible relation between that metal and Alzheimer's disease, aluminum is believed to be among the most biochemically inert metals. It has few, if any, proven adverse effects on human health. Iron is of course an essential and important micronutrient which is frequently added to foods and animal feeds for good nutrition. Also, iron and aluminum wastes are abundant at some biowaste sites and may be used in scrap form in PBTC's generated on-site to inactivate or neutralize a wide range of biomass constituents including interstitial, suspended or sorbed VC's and other noxious toxic vapors.

Zinc can be as effective as copper in some instances though its mechanisms of control seem somewhat different as do the treated end products. When used as the sole PBTC oligodynamic metal constituent against some biowastes, zinc leaves a sweet odor not characteristic of the treated biowaste and not encountered when copper and metal combinations are used. To some persons, this odor is not inoffensive. The addition of benzoic acid or p-dioxane synergistically increases the effectiveness of zinc.

Iron alone also leaves a somewhat characteristic odor after treatment of many biowastes. The odor is very mild and may be characterized as "earthy". Benzoic acid, benzaldehyde and p-dioxane also improve the effectiveness of iron in many cases.

Silver and zinc seem to exhibit primarily catalytic properties and to act as ion receptors for coordination complexes.

Silver is also effective in treating both N and S radicals to form coordination compounds which are relatively harmless compared to their precursors. Silver is in this respect particularly useful for complexing and precipitating the harmful constituents of biowaste liquids such as landfill leachates. Silver can advantageously be combined in cost effective trace amounts with one or more other metals, and its microbicidal properties may in many cases be used to advantage in stabilizing a biowaste.

Zirconium and aluminum have many similar or common properties as used in PBTC's and may be used almost interchangeably, particularly in halide form.

For most biowaste treatment applications, the best SR/P's known to be available at the present time are aldehydes. Aldehydes exhibit a wide range of beneficial reactions with biowastes substrates. Also, some aldehydes impart highly desirable odor profiles to treated biowastes. Furthermore, a combination of oligodynamically active silver and an appropriate aldehyde, synergized by the surfactant component of a PBTC, optimizes beneficial catalytic reactions and provides microbicidal control of harmful microorganisms. Aldehydes also provide excellent vapor-to-vapor reaction control of VC's and inorganic vapors evolved from biomass substrates.

Some wastes do require, for maximum effectiveness of the PBTC, that the aldehyde be augmented with a hydrocarbon solvent and a metallohalide complexing reagent such as benzoic acid or benzil.

The preferred aldehyde is benzaldehyde. That PBTC constituent is both a contact reactant and a vapor state reactant. It also endows many oligodynamic metals and oligodynamic metal halides with photosensitized activity which heightens the biowaste interaction capability of the PBTC. Benzaldehyde neutralizes and renders inoffensive a variety of nitrogen and sulfur compounds including primary, secondary and tertiary amines and ammonia. By cross-linking and polymerizing proteinaceous breakdown products, the aldehyde interdicts the breakdown products. Benzaldehyde frequently aids in biowaste substrate treatment as a catalyst. This effect is photochemically enhanced by sunlight. This coincides with normal treatment conditions for biowaste which is almost always treated out of doors.

Because of its ability to photoactivate and promote the catalytic activity of oligodynamic metals, the inclusion of benzaldehyde makes a PBTC particularly effective against some very difficult-to-treat biowaste species including many thiols, mercaptans and other organic sulfur compounds. Benzaldehyde also has the advantage of being an effective biowaste odor recharacterizer. It has a pleasant foundation aroma (oil of bitter almond) on which a pleasing and functional product odor can be structured.

An odor recharacterizer, whether or not based on an aldehyde constituent of a PBTC, is employed to impart an appealing odor to a biowaste or to restore an odor of pleasant character. Typical are "woodsy" and "earthy" odors for composts, "floral" odors for landfills, and "fresh and soapy" odors for hospital biowastes. Odor recharacterizers are used because some persons find "no odor at all" objectionable. Representative odor characterizers are mixtures containing beta-ionone, camphor, eucalyptus, citral oils, vanillin, and other odorants.

Benzaldehyde is also preferable from the viewpoints of safety and environmental protection. That benzaldehyde is safe is evidenced by the fact that this compound is edible. It is widely employed in the food industry as a flavorant. Benzaldehyde is also a naturally occurring component of many foods—cherries, peaches and almonds, to name but a few.

Furthermore, benzaldehyde is used in low concentrations in the PBTC's disclosed herein; and this compound typically reacts quickly with noxious constituents in the biowaste being treated to form harmless complexes or reaction products which are readily biodegraded. Also, the release of benzaldehyde into the environment is not of concern as it is quickly oxidized in ambient air to benzoic acid (which is GRAS).

There are numerous alternatives to benzaldehyde including acetaldehyde, glutaraldehyde, citral and decanal. The alternatives to benzaldehyde tend to have higher cost-to-effectiveness ratios or to be inferior in terms of activity and functions and as recharacterizers for treated biowastes.

Nevertheless, other SR/P's—particularly those identified above—can be substituted or added to benzaldehyde if the circumstances warrant, particularly if other photosensitizing constituents such as benzoic acid, benzil or benzoyl peroxide are included as components of the PBTC. Glutaraldehyde and anisaldehyde are also particularly acceptable for use alone or in combination with benzaldehyde.

Where vapor-to-vapor reaction is not quite so important as crosslinking of biowaste components, other compounds which may be used alone as a SR/P or in conjunction with one or more aldehydes are tannic acid, borax and borides.

PBTC's as disclosed herein tend to be more effective with particular pH ranges in the treatment zone. For example, in treating landfill leachates, a substrate pH range of from about 3.5 to about 10.5 is desirable while the preferred range is between 6.7 and 7.3. Compost is preferably treated in a pH range of about 5–8, though treatments are nevertheless still effective over a much wider pH range. For biowastes containing high concentrations of carboxylic acids, the preferred pH treatment range is about 6.5 to about 9.5. The preferred pH is about 8. For biowastes containing high dissolved concentrations of ammonia and other nitrogen compounds, a pH of from about 3 to 7 is desirable; and the preferred pH is 5.5. Sewage or sludge which contains high concentrations of proteinaceous matter is frequently, though not always, best treated at a low PBTC pH in the range of about 2 to 6. The preferred pH of PBTC for treating high protein materials is 5.5.

Biowastes high in sulfur may be treated at a pH ranging from about 6 to 14. The preferred pH, dependent somewhat on other biowaste constituents, is about pH 9. Waste water from fish processing can be treated at a pH ranging from about 3 to 9. Preferred is a pH of about 4.5. The treatment of biowastes with significant concentrations of carboxylic acids or terpenes by PBTC's containing aluminum halides is preferably effected at a pH of about 7 to 12. When glacial acetic acid is used as a solvent, the preferred pH is about 8.5. Use of other wetting agents or solvents may require higher pH's (on the order of pH 10 to 11).

If the biowaste is to be converted by PBTC action to an effective fermentation substrate, the pH may be varied in accord with the desired organism and fermentation objective. If simple cells for high protein production are required, for example, an inoculum of Candida torulopsis can be added to a biowaste substrate adjusted to pH of about 3.5. If fermentation for the production of alcohol is wanted, Saccharomyces cerevesiae or carlsbergensis at a pH of about 3.8 may be required. Important specific micronutrients essential to favoring the selected organism may also be provided by the PBTC.

The foregoing pH parameters can be obtained by selecting at least one TA/S which exhibits at least the generally desired pH range and by supplementing or incorporating an appropriate amount of an alkali or acid in the complex.

A PBTC can sometimes employ to advantage a combination of a surfactant and an oligodynamic metal which under normal conditions are antagonistic and cannot be uniformly distributed in a carrier such as water to form a homogeneous, single phase formulation. Instead, the formulation will separate into a liquid phase and a flocculent phase. This type of PBTC is referred to herein as a partition formula. Particular care is required in preparing a partition formula, and the addition of mediating or partitioning agents which suppress the antagonism during periods of intimate contact without destroying the synergistic functionality of the coingredients are typically required. The order in which ingredients are blended and the addition to the formula of what are referred to herein as a "partitioning agent", a "release retardant" and a "proton donor" are important.

An ammonium ion source such as aqueous ammonia (ammonium hydroxide) or a quaternary ammonium compound may be used as a partitioning agent. Ammonia, tetrasodium phosphate, sodium hexametaphosphate, and trisodium phosphate may be used as release retardants, provided that any of a number of suitable acids such as adipic, oxalic or citric is present.

The partitioning agent inhibits and thereby prevents donor/ligand coupling between the TA/S and the oligodynamic metal constituent. The wanted interference lasts until the partitioning agent concentration is reduced to a critical lower limit by dilution, reaction or evaporation or is increased beyond a critical upper level by concentration. At either point, the inhibited reactions will proceed, the PBTC constituents will separate and the PBTC will become ineffective. Therefore, if an antagonistic TA/S and OMS are employed, it is important that a level of partitioning agent between (typically) empirically determined upper and lower limits be maintained in the PBTC until the PBTC reaches and acts upon the biowaste being treated.

The release retardant simply retards the impending reaction between ionic antagonists above critical levels of relative concentration. Below critical levels of concentration, it may permanently disrupt the potential reaction.

A proton donor can often advantageously be added to the mixture of PBTC and partitioning agent or release retardant. The protons promote Lewis acid activation of cations which have been suppressed by either a reaction retardant or a partitioning agent. In the case of a suppressant the proton donor slowly overcomes the reaction retardant. Citric, hydrochloric, acetic, sulfuric and phosphoric acids are examples of useful proton donors. In the case of a partitioning agent the proton donor becomes effective when the concentration of the partitioning agent falls below a critical limit.

In a PBTC partition formula, the oligodynamic metal or source(s) and soft or distilled water are combined first. Then a partitioning agent and/or an ionic release retardant may be added to the mixture.

Once the oligodynamic metal constituent has been dispersed in the aqueous carrier and depotentiated by the partitioning agent or the combination of that constituent and the release retardant, one or more selected anionic, cationic, non-ionic, or amphoteric surfactants are added to the aqueous dispersion. Finally, the aldehyde or other SR/P plus odor characterizers and/or other adjuncts are added.

This type of PBTC is generally alkaline due to the presence of the partitioning agent. If the partitioning agent is diluted, evaporated, reacted with the substrate or overwhelmed by ions of the biowaste substrates when the PBTC is applied, as is almost always the case, the pH will drop, resulting in rapid activation of the PBTC.

A general formula for a partition PBTC follows:

Constituent

Oligodynamic metal(s) (elemental or metallohalide)

Water

Release retardant and/or partitioning agent

Proton donor

Surfactant (nonionic, cationic, anionic (preferred) and/or amphoteric)

Aldehyde(s)

Representative Adjuncts

Humectant

Antifoaming agent

Pest repellent

A PBTC comprised entirely of non-antagonistic constituents requires no components to protect ingredients against that interaction which leads to unwanted separation of the PBTC constituent. This type of product is referred to herein as a neutral PBTC. Such complexes will typically be based on one or more non-ionic surfactants.

There follows a representative general formula for a neutral PBTC:

Constituent

Oligodynamic metal

Water

Surfactant

Adjunct(s)

Water, a mostly optional ingredient of a PBTC, is employed for such diverse purposes as facilitating: the formulation of a homogeneous PBTC, the application of the PBTC by spraying and comparable techniques, and the penetration of the biowaste being treated. In applications such as those where water for dispersal and/or penetration is present at the treatment site or maximum concentration of the PBTC constituents is required, the aqueous carrier may be reduced to a minimum or even entirely omitted from the complex.

Several optional components believed at the present time to have the most potential (for both partition and neutral PBTC's) are discussed above. Of these, perhaps the most useful in most cases are: an odor recharacterizer; an enzyme; a nucleating agent; an insect and/or animal repellent; an insecticide; a rodenticide; constituents for forming a biowaste covering slurry of waste paper; a humectant; enzymes and a variety of waste digesting microorganisms. Enzymes such as ricinus lipase, glucose oxidase, trypsin and pepsin can be used to promote the decomposition of noxious and toxic biowastes into less or even totally harmless materials.

The constituents of PBTC's are employed as compaction aids to convert susceptible components of a biowaste to denser, less bulky forms or materials. This is important because reduction in bulk increases the storage capacity of the site where the biowaste is to be stored.

In many cases, compaction can also be promoted by using appropriate adjuncts. The biowaste in a landfill, for example, will typically include large amounts of bulk cellulosic materials. In this case, compaction may be promoted by incorporating either the enzyme cellulase or a microorganism such as Aspergillus niger or Trichoderma viride in the PBTC complex to catalyze the decomposition of the cellulosic materials and thereby reduce their bulk. Where higher temperatures may be encountered in the biowaste—such as in composting—the addition of Thielatia terrestris, a thermophilic soil fungus capable of producing cellulase and surviving at high temperatures, can be employed.

Repellents, insecticides and rodenticides keep disease vectors from the biowaste. Examples of repellents and insecticides which are compatible with the other components of PBTC's, available at acceptable cost, and otherwise suitable include: Warfarin, citronellol, borax, sodium tetrabromide, benzil, pyrethroids, pyrethrins, rotenone, sabadillia, ryania, chlorinated terpenes, malathion, spores of bacillus papillae, endrin, coumachlor, dicoumarol, dimethyl phthalate, 2-ethyl-1,3-hexanediol, and 2-phenylcyclohexanol.

Humectants attract moisture to and retain it in the PBTC/biowaste reaction zone, thereby facilitating many of the chemical reactions involved in sequestering, decomposing, complexing, and otherwise neutralizing and inactivating noxious and toxic components of the biowaste being treated. Where moisture control is required in a treated biowaste, addition to the PBTC of calcium chloride, a glycol or glycerol can be beneficial.

Plant nutrients, particularly micronutrients known to be deficient or absent from a particular biowaste, can be supplemented by considered selection of one or more PBTC ingredients leading to increased polyfunctionality of the complex. For example, in a geographical region where copper is deficient, a compound or complex of that metal may be selected as the oligodynamic metal source. Where zinc or iron are deficient, compounds or complexes of those metals may be selected. In other cases, iodine as a metallohalide complex, magnesium and other minerals can advantageously be added to the PBTC.

It was pointed out above that a PBTC may be employed in either a concentrated or diluted form. Representative diluents and the proportions in which they are typically employed are:

| Diluent soluent | Dilution Range |
|---|---|
| Water | from about 10 to 99.1% |
| Propylene glycol | from about 4 to 50% |
| Acetic acid | from about 3 to 20% |
| Ethyl or methyl alcohol | from about 1 to 25% |

These ranges of product dilution will normally be lowered by further dilution prior to or as a result of application of the PBTC to a biowaste. Dilution for or during application may range from about 10 to 1000 of diluent to one part of PBTC. The actual effective concentration of the PBTC in the biowaste substrate may range from about 10 to 5000 ppm based on the solids content of the biowaste substrate. Continued treatment ranges are on the order of 50–150 ppm of PBTC.

The examples which follow describe specific, representative formulations of the character discussed in detail above, the use of those formulations to treat a wide variety of biowastes and the positive results in the stabilization of the biowaste and the neutralization of VC's and noisome effluents that were obtained.

EXAMPLE I

This example shows that a simple PBTC with only two of the three primary constituents identified above can effectively neutralize and stabilize a simple biowaste such as some landfill leachates.

Formula 1

| Ingredient | Formulation: Percent |
| --- | --- |
| Silver nitrite | 3.00 |
| AEPD | 3.00 |
| Water (at about pH 7) | 94.00 |
|  | 100.00 |

Treatment:

The formula 1PBTC was employed in a ratio of 2 parts of PBTC to 1000 parts of biowaste to treat a leachate obtained from a seven year old sanitary landfill. The leachate had an unpleasant odor attributable to a high S/N volatiles profile, a result of offgases emanating from a mixture of ammoniacal and sulfide compounds. The leachate had a pH of 7.2 to 7.3 and 45,000 ppm of suspended solids.

Results:

The leachate solids precipitated as a dark gray sludge which had a very low detectable volatile profile and a volume about one-tenth that of the clear aqueous supernatant. The supernatant had essentially no odor and a solids concentration of approximately 500 ppm.

Result of IR, FID and GC. scans—numerous organic and inorganic compounds in the head space including 4 to 5 sulfur species; $H_2S$ positive.

In this test three samples were treated. Details of the results for each of these samples follow.

Sample 1

100 mls of leachate treated with approximately 0.2 mls of Formula 1.

1 min.—90% reduction in all volatiles.

5 min.—99% reduction in all volatiles.

Samples before treatment—turbid.

After treatment—clear with precipitate.

Sample 2

100 mls. treated with 0.2 mls of Formula 2 as for a comparison (see Example II below).

1 min.—50% reduction in all volatiles 5 min.—90% reduction in all volatiles

Samples before treatment—turbid.

After treatment—turbid.

Sample 3

1 mls. treated with 0.2 mls of Formula 1.

1 min.—80% reduction in all volatiles 5 min.—99% reduction in all volatiles *: Sample phased into two layers. Samples before treatment, turbid. After treatment, layered. Supernatant (90%)—clear, volatile presence=trace. Sediment (10%)—gray and thick, volatile presence=trace.

Responses to the application of the PBTC's were immediate in all three runs. In this regard, it will be appreciated that only very small amounts of the PBTC were added to the leachate, the goal being to confirm that the leachate could be promptly and effectively treated with the two-component PBTC. For continued stabilization of the leachate liquid and solid phases over an extended period of time, a higher dosage of the PBTC would be employed. Preferred are repeat applications—a high initial or shock dosage for immediate suppression and subsequent lower maintenance dosages to ensure stabilization until complete resolution of the biowaste constituents into non-harmful materials.

Formula 1 exhibits considerable photoactivity. When the PBTC was applied to the leachate under non direct ambient daylight, and then exposed to strong ambient daylight, the reaction was completed within 15 seconds. The results included a 99% reduction in vapor and immediate separation of the leachate into liquid and solid phases with a noticeable darkening of the solids. Only 0.1 ml of the PBTC was required to obtain the same overall effectiveness as the applications made in those runs discussed above; and the PBTC remained effective after 72 hours.

Noxious volatiles were sequestered. The supernatant can be pumped directly into a sewer line or used to wash down vehicles, for irrigation, and for other purposes not involving ingestion.

Sludge as generated in this test can be pumped onto a landfill for further concentration by evaporation and then incorporated into the landfill instead of being hauled to a toxic waste incinerator or dumped in and polluting a river, lake, or other body of water. Volatiles are sequestered, eliminating the adverse impact of high profile volatiles on the landfill site. The dried sludge is a space saving 6 to 12 times more concentrated than the leachate. As only one-tenth of the biowaste (the sludge) is sprayed onto the landfill for drying and storage, pumping costs are comparatively minimal.

It is in many cases advantageous to add an excess of the PBTC to a leachate. When the treated sludge phase of the leachate is subsequently sprayed onto the landfill, a PBTC loaded layer of material is formed as a cover on the existent landfill biowastes. This effectively and inexpensively supplies to the landfill the PBTC needed for treatment of the existent biowastes.

The treated sludge may also be mixed with liquified waste paper stock to form site coverings which are superior in various respects to the currently employed tarps, net and dirt.

EXAMPLE II

This example shows how a PBTC can be employed to effectively treat sewage.

Biowaste:

Municipal sewage (MSW) obtained from Waste Management Central Disposal, Pompano Beach, Fla.

The sewage was brown and dirt-like with a very strong odor of ammonia. The primary VC's were ammonia and a mixture of amines as determined by GC, FID, and IR (gas chromatograph, flame ionization detector and infrared) analysis.

The MSW was dispersed in water to emulate the sewage as it would be transferred through a sewage line and treated with the Formula 1 PBTC and a second PBTC formulated as follows:

Formula 2

| Ingredient | Percent |
| --- | --- |
| Water | 62.36 |
| *Methocel J75MS | 2.50 |
| Ammonium hydroxide | 5.00 |
| Copper Sulfate | 6.00 |
| Aluminum chlorohydrate | 3.00 |

| Ingredient | Percent |
| --- | --- |
| Sodium xylene sulfonate 40% | 12.00 |
| Benzaldehyde | 4.00 |
| Propylene glycol | 2.50 |
| Citric acid | 2.50 |
| Beta-Ionone | 0.07 |
| Fluorescent yellow | 0.07 |
| Total | 100.00 |

*Methocel J75MS is a carboxymethylcellulose available from Hercules Chemicals Company Inc.

Two runs were made. The particulars follow.
Run #1:
100 mls of a 5% MSW dispersion was treated with 1 ml of Formula 1. The sample was turbid before treatment.
Results:
1 min.—40% reduction in all volatiles.
5 min.—85% reduction in all volatiles.
9:1 ratio of supernatant to solids.
Run #2:
100 mls. of the 5% MSW solution was treated with 1 ml of Formula 2. The sample was turbid and dark brown before treatment.
Results:
1 min.—80% reduction in all volatiles.
5 min.—98% reduction in all volatiles.
The ratio of supernatant to solids was approximately 7:3.

In both runs, offgases responded immediately to treatment with the PBTC. Initial PBTC dosages of 0.2% were more than adequate to reduce the offgas profile to minimum olfactory detection levels.

In subsequent runs, Formula 2 showed a substantially greater effectiveness in treating dispersions with higher concentrations of MSW.

Preliminary analysis showed a spike reduction in ammoniacal volatiles of 85 percent in Run 1 and 95 percent in Run 2. The tests showed that Formula 2 is the preferred formula for the MSW and similarly composed biowastes.

Both treatments resulted in the formation of a sludge with some flocs. The supernatant water was suitable for reuse.

The sludge was in a high concentration, pumpable form suitable for agricultural use and for further concentration by evaporation. The nitrogen, sulfur, phosphorus and potassium content was about 10 to 20% higher in the sludge than in the untreated MSW, substantially enhancing the nutrient value and making the sludge useful for fertilization, composting and soil amendment.

Volatiles were effectively sequestered in both the supernatant and the sludge, eliminating pollution in the form of high profile volatiles and conserving valuable nutrients. Processing time of the sludge to compost was reduced by about 10 to 15%—a major economy in terms of cost of finished product and conservation of site capacity.

Initial shock dosages of about 500 to 1000 ppm are sufficient to achieve substantial reductions in and sequestration of VC'S and stabilization of the precipitated sludge. Ongoing treatments of 100 to 300 ppm or less are adequate to ensure continued stabilization with the exact amount depending on the makeup of the incoming material. Oversupplementation with the PBTC to convert the sludge to a carrier for an interactive compost or landfill interactive cover requires approximately 50% of the amount of PBTC used for shock treatment; i.e., 250 to 500 ppm.

Both formula 1 and formula 2 demonstrate the increased effectiveness provided by photosensitization of the PBTC.

In concentrated form, formula 2 changes color dramatically when exposed to visible light. The color shifts from blue or green to a silver tinged deep magenta.

Maximum overall effectiveness is obtained by combining the PBTC with the biowaste before exposure to direct light. The result, when the PBTC is thus added to biowaste substrates such as typical MSW leachates or to waste waters from food processing operations, is an overall reduction in usage providing the same effectiveness of no less than about 10% and as great as 50% or more.

The use of formula 2 under subdued lighting in duplicate tests followed by exposure to strong daylight produced an overall increase in effectiveness of 20%; and the required dosage was lowered by 10%. An 0.8 ml dose was 100% effective by the end of the first minute of treatment.

Formula 2 was also tested on the same leachate as Formula 1 (see Example I). The results were comparable except that some floccing was noticed in addition to precipitate formation, and the separation between the supernatant and the precipitate was not as sharp.

EXAMPLE III

Formula 3

Origin of Biowaste Material:
Boston, Mass.
Description of Material:
Sewage sludge (S/S); black and tar-like with a very strong fecal or rancid fatty acid odor.
Primary Volatiles:
Fatty acids, butyric acid
Analysis by:
GC, FID, and IR.

The S/S biowaste was treated with PBTC formulas 1, 4, and (EXAMPLES I, II, and IV) to provide a basis for comparison and with PBTC formula 3. The latter, which is described below, is an enhanced PBTC intended specifically for the treatment of sewage sludges and other biowastes with a high fatty acid profile.

| Ingredient | Percent |
| --- | --- |
| Water | 83.00 |
| Copper Sulfate | 4.00 |
| Aluminum chlorohydrate | 4.00 |
| Methocel J75MS | .80 |
| Ammonium Hydroxide | .05 |
| VWR 9N9 | 2.50 |
| Benzaldehyde | 3.00 |
| Amyl Acetate | .65 |
| Propylene Glycol | 2.00 |
| Total | 100.00 |

Run #1:
100 mls. of S/S was treated with 0.1 ml of formula 4. The sample was turbid before treatment.
Results:
1 min.—40% reduction in all volatiles.
5 min.—70% reduction in all volatiles.
Floc to supernatant ratio of about 7:3.
Run #2:
100 mls of the 5% S/S dispersion was treated with 1 ml of formula 1. The sample was turbid before treatment.
Results:
1 min.—30% reduction in all volatiles.
5 min.—50% reduction in all volatiles. Solids to supernatant ratio: 9:1.

Run #3:

100 mls of the 5% S/S dispersion was treated with 1 ml of formula 5. The sample was turbid before treatment.
Results:
1 min.—80% reduction in all volatiles.
5 min.—80% reduction in all volatiles.
Run #4:
100 mls of the 5% S/S solution was treated with 1 ml of formula 3. The sample was turbid before treatment.
Results:
1 min.—80% reduction in all volatiles.
5 min.—98% reduction in all volatiles.

The results of and benefits of the just-described treatments with Formula 3 were comparable to those described in EXAMPLE II.

Formula 3 was also very effective against MSW. Due to the presence of volatile carboxylic acid decomposition products, MSW treated with the metallohalide-lacking PBTC formula 1 was significantly more odorous than the formula 3-treated MSW.

As discussed above, PBTC formula 3 is designed for the optimal treatment of biowastes dominated by short chain fatty acids. These materials are encountered in many industrial settings and in some exogenous sites. Formula 3 very effectively neutralizes the biowastes associated with all of the following and many other biowastes and biowaste-associated and generating processes and equipment, including:

DAF cells

Biowaste digesters

Storage containers

Biowaste windrows and piles of biowastes

Biowaste lagoons

High fatty acid content production wastes

Fat sumps in restaurants and institutions

Other specific applications in which formula 3 is very effective include: septic tank, Port-a-Potty, and pet litter treatment; kennel and sump washdown; garbage container rinsedown; toilet, bedpan and carpet cleaning; and compost pile, diaper, boat and holding tank deodorization.

Formula 3 can be employed to advantage in the airline, marine, passenger ship, hospital and other industries in which there are apt to be people in the immediate vicinity of the biowaste being treated.

Biowastes which can be effectively treated with formula 3 and comparable PBTC complexes include:

Vomitus

Garbage

Solid wastes

Human wastes

Animal wastes

Compost

Fish offal

Food wastes

Medical wastes

Formula 3-like complexes are particularly effective against fecal matter, which is usually dominated by amines. This remains true even in those applications involving raw sewage where the dominant mass is alkaline. The exception seems to involve those instances where a high fat diet or disease has given the fecal matter a high lipid profile and those instances where the fecal matter is mixed with vomitus or other materials with an acidic profile.

When a microbicide is required—for example, in treating human wastes in an aircraft or other holding tank—silver, aldehydes, biocidally active surfactants such as quaternary ammonium compositions and halides may be added to or increased in concentration in the PBTC.

EXAMPLE IV

Description of Material:
Agricultural lagoon water (dairy livestock wastes).
Primary Volatiles:
Ammonia; primary, secondary, tertiary amines; sulfur compounds; carboxylates.
Analysis by: GC, FID and IR.

The agricultural lagoon water was treated with PBTC formulas 5 (EXAMPLE V) and 9 (EXAMPLE XIII) as a basis for comparison and with PBTC Formula 4 which was formulated as follows:

Formula 4

| Constituent | Percent |
|---|---|
| Bentonite Clay* | 10.00 |
| Sodium Hypochlorite (8% Solution) | 10.00 |
| Ferrous Sulfate | 5.00 |
| Copper Sulfate | 2.00 |
| Benzaldehyde | 2.00 |
| Van Wet 9N9 (Nonionic Surfactant)** | 5.00 |
| Water | 66.00 |
| Total | 100.00 |

*Bauxite, fuajistite, montmortilite alunite or other aluminum or iron ion source and the like may be used interchangeably.
**Lignin sulfonate may replace at least part of the Van Wet surfactant in formulations intended for application to livestock wastes.

Run #1:
100 mls of the lagoon water was treated with 1 ml of formula 9. The sample was turbid before treatment
Results:
1 min.—75% reduction in all volatiles.
5 min.—95% reduction in all volatiles.
Run #2:
100 mls of the lagoon water was treated with 1 ml of formula 4. The sample was turbid before treatment.
Results:
1 min.—80% reduction in all volatiles.
5 min.—98% reduction in all volatiles.
Run #3:
100 mls of the lagoon water was treated with 1 ml of formula 5. The sample was turbid before treatment.
Results:
1 min.—80% reduction in all volatiles.
5 min.—80% reduction in all volatiles.

The results were similar to those reported in EXAMPLES II and III except that the retention of valuable total nitrogen, sulfur, phosphorus and potassium was higher—on the order of 30% greater retention of nitrogen and sulfur and about 10 to 12% greater retention of phosphorous.

EXAMPLE V

Comparably increased retention of valuable nutrients was found in other applications of the PBTC described in EXAMPLE II (formula 2) to dairy cow wastes and in the treatment of other biowastes with both formula 2 and formula 3. The data is presented in Table 1. The data in that table reports N as total nitrogen (TN), S as total sulfur (TS), and volatiles as total odorous/inodorous volatiles (TV) in the head space of containers with treated and untreated samples;

TABLE 1

| Sample | TN | TS | TV | Mg/L BOD* mg/L |
|---|---|---|---|---|
| Dairy cow waste Washdown (primary lagoon) | | | | |
| Control | ~2.7% | ~0.9 | 335 ppm | 1,570 |
| Treated Sample(1) | ~4.3% | ~1.3 | 13 ppm | 450 |
| Settling lagoon | | | | |
| Control | ~2.2 | ~0.8 | 200 ppm | 670 |
| Treated Sample(2) | ~4.1 | ~1.3 | 5 ppm | 120 |
| Poultry process waste water | | | | |
| Control | ~4.1 | ~1.8 | 400 ppm+ | 1,740 |
| Treated Sample(3) | ~5.3 | ~2.3 | 21 ppm | 540 |
| Compost (non-legumous) | | | | |
| Control | ~3.2 | (0) | 290 ppm | 1,100 |
| Treated Sample(4) | ~4.7 | (0) | 16 ppm | 320 |
| Composted sewage | | | | |
| Control | ~2.6 | ~0.37 | 150 ppm | 950 |
| Treated Sample(5) | ~3.5 | ~0.65 | 5 ppm | 100 |

*BOD = Biological Oxygen Demand

Samples Nos. 1 and 2 were treated with PBTC formula 2. Sample No. 3 was treated with formula 4. Samples 4 and 5 were treated with formula 3. The rate of treatment was 250 to 275 ppm of PBTC, dry weight.

Supernatant water from aftertreatment settling was exposed to a 48 watt, 2357 Å UV source at a rate of 5 gallons per minute. The UV-treated water exhibited better clarity, fewer suspended solids (less than 200 ppm), no BOD and no detectable volatiles when examined with a scanning infrared analyzer and a gas chromatograph. The treatment was also more economical.

EXAMPLE VI

Formula 5

| Ingredient | Percent |
|---|---|
| Water | 63.83 |
| Beta Ionone | 0.07 |
| NH$_4$OH | 5.00 |
| Citric Acid* | 5.00 |
| Copper Sulfate/Chloride** | 4.10 |
| Van Wet 9N9 | 9.00 |
| Exxon Cationic Surfactant*** | 9.00 |
| Benzaldehyde | 4.00 |
| Total | 100.00 |

*Benzoic acid, benzoyl peroxide and benzil may be substituted in whole or part for the citric acid, particularly in PBTC's designed for treatment of substrates containing significant concentrations of hydrocarbons.
**The OMS may range from about 5 to 75%. Preferred is about 25% of the oligodynamic metal.
***Ethanol may be substituted for the surfactant in an amount ranging between about 2 and 12% of the formulation. Preferred is a substitution of about 5%.

EXAMPLE VII

Sanitary landfills present a particular challenge because of the variety of biowastes found in them. Nevertheless, the biowastes at these and comparable sites can be effectively neutralized and stabilized with PBTC's. One formula for a neutral complex optimal for this application (formula 5) was set forth above. The following formula is one basic example of partitioned PBTC formulated for use at landfills and in other applications involving a variety of biowastes with different characteristics.

| Constituent | Percent |
|---|---|
| Surfactant (anionic, cationic nonionic, amphoteric or mixture thereof) | 1.0–99 |
| Oligodynamic metal(s)* | 0.5–85 |
| Polymerizer/cross-linking reactant/synergist (aldehyde) | 0.1–80 |
| Halide/metallohalide | 0.1–75 |
| Proton donor (citric acid, hydrochloric acid, etc.) | 0.0–35 |
| Partitioning agent (ammonium ion) | 0.0–25 |
| Odor recharacterizer | 0.0–25 |

*May be any preferred oligodynamic metal source including a halogen compound or complex.

Additives may be employed in the complex to improve its effectiveness for selected biowastes. Such additives include borax, ferric ion, lignin sulfonate and betaine.

PBTC's of the character described in this example and other of the PBTC's disclosed herein can also be employed to advantage to control odors associated with organic fertilizers applied to fields, pastures, lawns and other areas. In this case, it may be advantageous to mix the PBTC with the fertilizer before the fertilizer is applied, typically in a proportion ranging from 10 ppm to 10,000 ppm dry weight of the PBTC.

EXAMPLE VIIA

The PBTC of Example VII may also be added to a slurry comprised of a suitable biodegradable barrier forming material such as ground waste paper, pulped fibers or comparable cellulosic material and then cast onto the surface of a biowaste to provide interactive barriers which make harmless offvapors from the biowaste.

One suitable formulation for an interactive biowaste barrier or cover is:

| Constituent | Preferred (percent) | Range (percent) |
|---|---|---|
| Chopped or milled paper or comparable cellulosic material | 6.0 | 4–9 |
| Water | 92.0 | 90–95 |
| PBTC | 1.0 | 0.1–3 |

The cellulosic material is ground into particles ranging in size from an average of 10 to 150 mesh (usually, the finer, the better). The paper and water (preferably warm or hot, 40°–70° C.) are added to any suitable mixer—a concrete or paddle type—and agitated vigorously until the paper becomes pulped (generally about 30 minutes). The Example VII PBTC is added and the mixing continued for at least an additional 30 minutes. The slurry, which will take on a foamy texture, is pumpable and may be spread by a spray head over biowaste to a depth of between 1.25" and 1.5" (0.75" is preferred). After a few minutes, the foamed product will settle and take on a visibly fibrous texture similar to freshly formed felt. Upon drying, a thin, strong interactive layer will remain. Depending on ambient weather conditions and thickness of application, drying will require from about an hour to several hours more.

The barrier will react with biowaste beneath or added onto it and will reactively intercept any fugitive emissions from underlying biowaste. Water from sprinkling or rain will transfer some of the Example VII PBTC from the interactive barrier into outer layers of the biowaste. This method and product will extend the interactive zone deeper into underlying biowaste. Ultimately, any unreacted portion will favorably influence leachates.

The interactive barrier formed from this formulation is easily applied and forms an excellent, tough and durable interactive barrier which will not be disturbed by wind. It takes up very little space which is more than offset by additional compaction of the underlying biowaste in response to the compaction provided by PETC and PBTC leaching. Insect and pest repellents or poisons may be added optionally as can dyes and other adjuncts.

EXAMPLE VIII

PBTC's may be diluted with water and used for cleaning and washing down surfaces contaminated with biowastes while simultaneously stabilizing the wastes. The stabilizing of the waste solids and elimination of VC's and their odors during the clean-up are noticeable immediately. When employed in this way, concentrated (undiluted) PBTC's are preferred.

PBTC's may also be used in air scrubbing devices to good effect. A concentration in the range of from about 0.01 to 50% of PBTC based on the volume of a scrubbing medium such as water can be used. A concentration of about 5% is preferred.

A PBTC can also be injected directly as an aerosol or spray into a duct or plenum carrying biowastes or biowaste-associated volatiles. The level of application can be from about 0.1 to 100% based on the biowaste. A 50% concentration of PBTC in a carrier such as water or propylene glycol is preferred.

The following formula is representative of those currently considered optimal for the cleaning and scrubbing, biowaste stabilizing applications just described.

| Constituent | Percent |
|---|---|
| Copper sulfate | 4.00 |
| Aluminum chlorohydrate solution | 5.00 |
| Ammonium hydroxide | 0.50 |
| Citric acid* | 3.00 |
| Exxon 9NM Amphoteric | 15.00 |
| Van Wet 9N9 | 15.00 |
| Benzaldehyde | 4.00 |
| Water | 53.50 |
| Total | 100.00 |

*All or part of the citric acid can be replaced with sodium citrate.

Formulation Protocol:

1. To 10 mls of water add ammonium hydroxide and agitate.

2. Add to the above mixture the aluminum chlorohydrate solution. The solution turns cloudy.

3. Add citric acid and agitate until the acid is completely dissolved and the solution is clear.

4. Add copper sulfate/chloride followed by the remaining water.

5. While gently agitating the solution, add the Van Wet 9N9 surfactant, mixing until the Van Wet is fully dispersed.

6. Add the Exxon 9NM in the same manner as the Van Wet.

7. Add the benzaldehyde while agitating the solution. The solution clouds momentarily until the benzaldehyde reacts in the formulation at which point the formula will clarify.

EXAMPLE IX

Enhanced biocidal activity is often a desirable attribute of a PBTC intended for institutional use. This minimizes the possibility of bacterial contamination.

One representative PBTC formulated to provide such enhanced microbicidal activity is the following:

| Ingredient | Percent |
|---|---|
| Benzaldehyde | 2.50 |
| Glutaraldehyde | 3.00 |
| Copper chloride dihydrate | 4.00 |
| Aluminum chloride | 3.00 |
| Silver chloride | 2.50 |
| Ammonium hydroxide | 2.00 |
| Quaternary ammonium compound | 15.00 |
| Citric acid | 2.00 |
| Ethyl alcohol | 2.50 |
| Eucalyptus | 0.70 |
| Camphor | 0.70 |
| Methyl salicylate | 0.70 |
| Pine oil | 5.00 |
| Soft water | 56.40 |
| Total | 100.00 |

In this formulation, the alcohol functions as a solvent for other organic constituents of the PBTC. It also acts as a solvent for lipids, fatty acids, hydrocarbons and other common biowaste constituents, thereby promoting the effectiveness of the PBTC.

In addition to its function as an odor characterizer, the pine oil functions as a solubilizer for biowaste components, a biocide, a penetration agent, a secondary surfactant and an odor recharacterizer.

The preferred quaternary ammonium compound is benzalkonium chloride, which provides a high degree of antisepsis.

In a representative application, the foregoing PBTC is added directly to fresh toilet wastes in a concentrated form as discussed above or diluted and then added. For treating toilet wastes Formula 5a is diluted with from about 0.2 to 50% water and added to the waste in a concentration of approximately 0.1 to 5.0%.

This PBTC formulation stabilizes toilet biowastes by interacting with proteins and protein breakdown products including peptones, polypeptides and amines. It also interacts with other nitrogen-containing compounds, with sulfur-containing compounds and with lipids and lipid breakdown products including fatty and other carboxylic acids. It neutralizes volatiles and inhibits volatile evolving chemical processes. It interacts with and stabilizes microbial populations and concentrates solids in the biowaste.

Formula 5a is also of importance because it demonstrates the capability that PBTC's have to effectively perform their expected multiplicity of functions and such additional tasks as may be required or desirable in particular applications of the invention.

EXAMPLE X

PBTC's can of course also be employed to advantage around the home to clean and disinfect and to stabilize garbage and other biowastes. One PBTC, formulated specifically for household and other uses with similar demands, is the following:

| Ingredient | Percent |
| --- | --- |
| Copper sulfate | 4.00 |
| Ammonium Hydroxide | 5.00 |
| Atlas G-3300 anionic surfactant | 12.00 |
| Propylene glycol | 1.50 |
| Benzaldehyde | 1.00 |
| Amyl acetate | 0.50 |
| Citric acid | 3.00 |
| Hard water | 73.00 |
| Total | 100.00 |

EXAMPLE XI

The following formulation is designed for treatment of cellulosic and other absorptive biowastes and for absorption into carriers subsequently usable for floating and other biowaste stabilizing and neutralizing covers.

| Ingredient | Percent |
| --- | --- |
| Water | 86.00 |
| Copper Sulfate | 4.50 |
| VAN WET 9N9 | 6.00 |
| Benzaldehyde | 1.50 |
| Propylene Glycol | 2.00 |
| Total | 100.00 |

Typically, this PBTC is employed at a rate of 10 to 1000 ppm (undiluted basis) calculated on the dry weight of the biowaste solids.

EXAMPLE XII

Formula 7

| Ingredient | Percent |
| --- | --- |
| Bromine as 1-bromo-3 chloro-5 dimethyldantoin | 5.00 |
| Aluminum chlorohydrate, 50% solution | 5.00 |
| Glacial acetic acid, propylene glycol or alcohol | 2.00 |
| Hard water | 88.00 |
| Total | 100.00 |

As was indicated above, many PBTC's are typically not particularly active against composts (and other wood-containing biowastes) because of the terpenes and related $C_{10}$ compounds found in significant concentrations in many woods. Formula 7 PBTC is in contrast highly effective in neutralizing and stabilizing biowastes in which significant concentrations of $C_{10}$ organic compounds are present.

EXAMPLE XIII

The preceding examples focus primarily on the use of PBTC's to decompose, sequester, complex or otherwise neutralize or inactivate biowaste components in a manner which keeps noxious and toxic components from evolving as the biowaste continues to decompose and to render harmless malodors released from the biowaste during the treatment process. In sanitary landfill and other applications, a perhaps equally important goal is to neutralize toxic leachates and/or other exudates while the biowaste is being stabilized.

Example I discloses a PBTC which can be employed to neutralize leachates of a toxic or noxious character. The following PBTC formulations have this capability and, also the ability to stabilize biowastes in a manner which suppresses the generation and release of exudates from biowaste.

Formula 9

| Ingredient | Percent |
| --- | --- |
| Copper sulfate | 4.00 |
| Aluminum chlorohydrate | 5.00 |
| Benzaldehyde | 1.50 |
| Glutaraldehyde | 2.50 |
| Citric acid | 2.00 |
| Van Wet 9N9, nonionic surfactant | 13.00 |
| Ammonium hydroxide | 0.17 |
| Water | 71.83 |
| Total | 100.00 |

PBTC's destined for biowastes with high concentrations of fatty acids require slight modifications of Formula 9. In particular, Formula 9 is diluted about 5:1 with water; and small additions of benzaldehyde, a halide and aluminum are made. Results are excellent with 9:1 solids reductions and volatile reductions in the 99 percent range consistently being achieved. Olfactory tests show no noticeable offgas odor.

EXAMPLE XIV

One representative PBTC described above (formula 7) is a basic concentrate which can be used to treat mixed ion biowaste wastes such as those found at sanitary landfills. Two other PBTC's which can be employed for this purpose and also to advantage to stabilize active composts are formulated as follows, Formula 12

| Ingredient | Percent |
| --- | --- |
| Van Wet 9N9 | 80.00 |
| Aluminum bromohydrate (Oligodynamic metal source) | 11.00 |
| Benzaldehyde | 9.00 |
| Beta-ionone (floral odor) | 0.0005 |
| Total | 100.00 |

Formula 14

| Ingredient | Percent |
| --- | --- |
| Aluminum bromohydrate | 11.00 |
| Ammonium hydroxide | 1.00 |
| Atlas G-3300 surfactant | 69.00 |
| Benzaldehyde | 8.95 |
| β-Ionone | 0.05 |
| Citric acid | 10.00 |
| Total | 100.00 |

EXAMPLE XV

It was pointed out above that PBTC's may be advantageously employed by adding the PBTC directly to a fluid effluent (EXAMPLE IV) or utilizing it as a scrubbing medium (EXAMPLE VIII), Another PBTC that can advantageously be employed in either of these modes is the following one.

Formula 16

| Ingredient | Percent |
| --- | --- |
| Aluminum hydroxide | 12.75 |
| Ferric chloride | 12.75 |
| Ammonium hydroxide | 3.00 |
| Atlas G-3300 anionic surfactant | 9.80 |
| Total | 100.00 |

EXAMPLE XVI

Described in this example is another representative PBTC which is particularly effective in treating pulp and paper processing effluents and other biowastes with high concentrations of sulfur compounds. This PBTC is formulated as follows:

Formula 17

| Ingredient | Percent |
| --- | --- |
| Sodium silicate | 51.90 |
| Aluminum hydroxide | 12.75 |
| Ferric chloride | 12.75 |
| Blend and add: | |
| Ammonium hydroxide | 3.00 |
| Anionic surfactant | 9.80 |
| Benzaldehyde | 9.80 |
| Total | 100.00 |

All or part of the oligodynamic metal sources in formula 17 may be replaced by a cupric or zinc ion source and/or a metal halide such aluminum bromide or aluminum chloride. A silver ion source may also be included as this metal is particularly effective in neutralizing sulfur constituents of pulp, paper and similar biowastes.

Also, aluminum sulfate may be used in place of a listed OMS if the PBTC is to be used where high concentrations of nitrogen and sulfur compounds and few if any carboxylic compounds are present. Zinc sulfate or zinc chloride may be used for biowastes loaded with fecal matter.

A partitioning agent and/or a proton source may be necessary with some combinations of surfactant and oligodynamic metal(s) in a formula 17-like complex so that they will properly combine.

Formula 17 is designed primarily for the treatment of acidic, sulfur-containing volatiles. These malodorous, typically very volatile substances can be very difficult to deal with under field conditions as they are somewhat resistant to broad spectrum treatment.

Formula 17 is very effective against noxious, toxic, volatile odor sources as pulp liquors, skunk scent, decomposing vegetation, methyl and ethyl mercaptans, thiols, hydrogen sulfide and some sulfur-based solvents. The overall effectiveness is about 90 percent as demonstrated by odor panels and confirmatory IR tests.

EXAMPLE XVII

The use of horse or other manure for mushroom bedding is exemplary of the desirable productive uses that can be made of what would otherwise be another bulk biowaste.

This example shows how all biowastes should be dealt with—used to provide benefits which more than compensate for hauling and treatment, producing an overall impact which is profitable to society.

Mushroom growers are increasingly viewed as community nuisances due to the hauling, handling and use of mushroom bedding comprised of manure. These problems are serious in many areas, increasing operational and legal costs and public pressures for such operations to relocate.

The product is unsightly and exhibits unpleasant volatile emanations which limit its use and, of course, deplete basic values unnecessarily. Also, spent mushroom bedding is somewhat limited for consumer use due to continued noxiousness which imposes limits on the home gardener. Even so, after use for mushroom production, the spent bedding is sold and constructively used by some gardeners.

The problems are significantly reduced or even eliminated by first treating the bedding with a PBTC in accord with the principles of the present invention.

In one representative demonstration, bedding comprised of horse manure, straw and spawn of Agaricus campestris was arranged into two windrows about 25 feet long by 4 feet wide by 3 feet high in an enclosed barn.

One row of bedding was sprayed, using a standard 2.52 gallon pressurized pump sprayer filled with 2 gallons of formula 5 diluted 50 to 1 with tap water.

The bedding was sprayed with 2 gallons of the diluted formula 5 over its entire exposed surface three times, each treatment being 5 days apart.

Immediate results on the treated vs. untreated bedding as judged by a panel of 12 people were unanimous;

Treated: little or no unpleasant smell.

Untreated: strong manure/ammonia smell.

Results on spent bedding were very similar.

Treated: little or no smell.

Untreated: manure/musty smell.

These tests were repeated on 5 separate occasions.

More surprising was the increased mushroom yield of treated over untreated bedding. In all tests the increased yield of mushrooms ranged from a low of 5 percent to a high of 8 percent.

The following formulas are representative of those currently considered optimal for cleaning and scrubbing, biowaste stabilizing applications.

EXAMPLE XVIII

| Constituent | Preferred Percent | Allowed Range |
| --- | --- | --- |
| Copper sulfate | 4.00 | 0.5–85 |
| Aluminum chlorohydrate solution* | 5.00 | 0.5–85 |
| Ammonium hydroxide | 0.50 | 0–25 |
| Citric acid** | 3.00 | 0–35 |
| Benzaldehyde | 4.00 | 0.1–75 |

| Constituent | Preferred Percent | Allowed Range |
|---|---|---|
| Water | 83.50 | 0–80 |
| Total | 100.00 | |

*The aluminum source can be either dry or in solution.
**All or part of the citric acid can be replaced with sodium citrate.

Formulation Protocol:

1. To 10 mls of water add ammonium hydroxide and agitate.
2. Add to the above mixture the aluminum chlorohydrate. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

For Examples XVIII through XXXIX, metals can be used up to their maximum saturation at room temperatures. For example, copper sulfate will form a 33% solution; aluminum chlorohydrate will form a 50% solution; and aluminum chloride will form a 52% solution. Exceeding these limits is possible, but the excess will not be soluble and will require agitation prior to application to the biomass being treated.

Water soluble aldehydes are readily soluble in metallic solutions; additions of surfactants in this case provide increased surface activity with the biomass. Also, mixed aldehydes are also beneficial for particular waste streams, such as in portable toilets. Note that if ring aldehydes are used without surfactants, the composition will separate upon standing and agitation will be required prior to application to treat a biomass. Ring aldehydes (normally aromatic) are at best only miscible in water solutions and therefore require additions of surfactant for formula stability and increase surface activity.

Additions of surfactant preferably should be reduced to the minimum necessary for formula stability and adequate surface activity, and in general should not exceed 30% of total formula weight. It is not essential that the surfactants be combinations of non-ionic and amphoteric. Either one is adequate, but the total surfactant amount must be sufficient to provide the necessary surface activity and formula stability. In some instances it is beneficial to use a cationic surfactant, which is known to provide antimicrobial properties, such as in portable toilets. In some instances it is beneficial to combine cationic and amphoteric surfactants.

EXAMPLE XIX

| Constituent | Preferred Percent | Allowed Range |
|---|---|---|
| Copper sulfate | 4.00 | 0.5–85 |
| Aluminum sulfate solution* | 5.00 | 0.5–85 |
| Ammonium hydroxide | 0.50 | 0–25 |
| Citric acid** | 3.00 | 0–35 |
| Benzaldehyde | 4.00 | 0.1–75 |
| Water | 83.50 | 0–80 |
| Total | 100.00 | |

*The aluminum source can be either dry or in solution.
**All or part of the citric acid can be replaced with sodium citrate.

Formulation Protocol:

1. To 10 mls of water add ammonium hydroxide and agitate.
2. Add to the above mixture the aluminum sulfate. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XX

| Constituent | Preferred Percent | Allowed Range |
|---|---|---|
| Copper sulfate | 4.00 | 0.5–85 |
| Aluminum chloride solution* | 5.00 | 0.5–85 |
| Ammonium hydroxide | 0.50 | 0–25 |
| Citric acid** | 3.00 | 0–35 |
| Benzaldehyde | 4.00 | 0.1–75 |
| Water | 83.50 | 0–80 |
| Total | 100.00 | |

*The aluminum source can be either dry or in solution.
**All or part of the citric acid can be replaced with sodium citrate.

Formulation Protocol:

1. To 10 mls of water add ammonium hydroxide and agitate.
2. Add to the above mixture the aluminum chloride. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXI

| Constituent | Preferred Percent | Allowed Range |
|---|---|---|
| Copper sulfate | 4.00 | 0.5–85 |
| Zinc sulfate solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:

1. To 10 mls of water add ammonium hydroxide and agitate.
2. Add to the above mixture the zinc sulfate solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify.

(However, water soluble aldehydes will not cloud when added.)

EXAMPLE XXII

| Constituent | Preferred Percent | Allowed Range |
| --- | --- | --- |
| Copper sulfate | 4.00 | 0.5–85 |
| Zinc chloride solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the zinc chloride solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXIII

| Constituent | Preferred Percent | Allowed Range |
| --- | --- | --- |
| Copper sulfate | 4.00 | 0.5–85 |
| Zinc acetate solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the zinc acetate solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXIV

| Constituent | Preferred Percent | Allowed Range |
| --- | --- | --- |
| Copper sulfate | 4.00 | 0.5–85 |
| Copper chloride solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the copper chloride solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXV

| Constituent | Preferred Percent | Allowed Range |
| --- | --- | --- |
| Copper sulfate | 4.00 | 0.5–85 |
| Titanium sulfate solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the titanium sulfate solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXVI

| Constituent | Preferred Percent | Allowed Range |
| --- | --- | --- |
| Copper sulfate | 4.00 | 0.5–85 |
| Titanium trichloride solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:

1. To 10 mls of water add ammonium hydroxide and agitate.
2. Add to the above mixture the titanium trichloride solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXVII

| Constituent | Preferred Percent | Allowed Range |
|---|---|---|
| Copper sulfate | 4.00 | 0.5–85 |
| Zirconium chloride solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:

1. To 10 mls of water add ammonium hydroxide and agitate.
2. Add to the above mixture the zirconium chloride solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXVIII

| Constituent | Preferred Percent | Allowed Range |
|---|---|---|
| Copper sulfate | 4.00 | 0.5–85 |
| Zirconium sulfate solution | 5.00 | 0.5–85 |
| Ammonium hydroxide | 0.50 | 0–25 |
| Citric acid* | 3.00 | 0–35 |
| Benzaldehyde | 4.00 | 0.1–75 |
| Water | 83.50 | 0–80 |
| Total | 100.00 | |

*All or part of the citric acid can be replaced with sodium citrate.

Formulation Protocol:

1. To 10 mls of water add ammonium hydroxide and agitate.
2. Add to the above mixture the zirconium sulfate solution. The solution turns cloudy.
3. Add citric acid and agitate until the acid is completely dissolved and the solution is clear.
4. Add the remaining water.
5. Add the benzaldehyde while agitating the solution. The solution clouds momentarily until the benzaldehyde reacts in the formulation at which point the formula will clarify. (However, water soluble aldehydes will not cloud when added.)

EXAMPLE XXIX

| Constituent | Preferred Percent | Allowed Range |
|---|---|---|
| Copper sulfate | 4.00 | 0.5–85 |
| Aluminum chlorohydrate solution* | 5.00 | 0.5–85 |
| Ammonium hydroxide | 0.50 | 0–25 |
| Citric acid** | 3.00 | 0–35 |
| Glyoxal | 4.00 | 0.1–75 |
| Water | 83.50 | 0–80 |
| Total | 100.00 | |

*The aluminum source can be either dry or in solution.
**All or part of the citric acid can be replaced with sodium citrate.

Formulation Protocol:

1. To 10 mls of water add ammonium hydroxide and agitate.
2. Add to the above mixture the aluminum chlorohydrate. The solution turns cloudy.
b 3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXX

| Constituent | Preferred Percent | Allowed Range |
|---|---|---|
| Copper sulfate | 4.00 | 0.5–85 |
| Aluminum sulfate solution* | 5.00 | 0.5–85 |
| Ammonium hydroxide | 0.50 | 0–25 |
| Citric acid** | 3.00 | 0–35 |
| Glyoxal | 4.00 | 0.1–75 |
| Water | 83.50 | 0–80 |
| Total | 100.00 | |

*The aluminum source can be either dry or in solution.
**All or part of the citric acid can be replaced with sodium citrate.

Formulation Protocol:

1. To 10 mls of water add ammonium hydroxide and agitate.
2. Add to the above mixture the aluminum sulfate. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXI

| Constituent | Preferred Percent | Allowed Range |
|---|---|---|
| Copper sulfate | 4.00 | 0.5–85 |
| Aluminum chloride solution* | 5.00 | 0.5–85 |
| Ammonium hydroxide | 0.50 | 0–25 |
| Citric acid** | 3.00 | 0–35 |
| Glyoxal | 4.00 | 0.1–75 |

| Constituent | Preferred Percent | Allowed Range |
|---|---|---|
| Water | 83.50 | 0–80 |
| Total | 100.00 | |

*The aluminum source can be either dry or in solution.
**All or part of the citric acid can be replaced with sodium citrate.

Formulation Protocol:
1. To 10 mls of water add ammonium hydroxide and agitate.
2. Add to the above mixture the aluminum chloride. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXII

| Constituent | Preferred Percent | Allowed Range |
|---|---|---|
| Copper sulfate | 4.00 | 0.5–85 |
| Zinc sulfate solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the zinc sulfate solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXIII

| Constituent | Preferred Percent | Allowed Range |
|---|---|---|
| Copper sulfate | 4.00 | 0.5–85 |
| Zinc chloride solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the zinc chloride solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXIV

| Constituent | Preferred Percent | Allowed Range |
|---|---|---|
| Copper sulfate | 4.00 | 0.5–85 |
| Zinc acetate solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate,
2. Add to the above mixture the zinc acetate solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXV

| Constituent | Preferred Percent | Allowed Range |
|---|---|---|
| Copper sulfate | 4.00 | 0.5–85 |
| Copper chloride solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the copper chloride solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXVI

| Constituent | Preferred Percent | Allowed Range |
| --- | --- | --- |
| Copper sulfate | 4.00 | 0.5–85 |
| Titanium sulfate solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the titanium sulfate solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXVII

| Constituent | Preferred Percent | Allowed Range |
| --- | --- | --- |
| Copper sulfate | 4.00 | 0.5–85 |
| Titanium trichloride solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the titanium trichloride solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXVIII

| Constituent | Preferred Percent | Allowed Range |
| --- | --- | --- |
| Copper sulfate | 4.00 | 0.5–85 |
| Zirconium chloride solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the zirconium chloride solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

EXAMPLE XXXIX

| Constituent | Preferred Percent | Allowed Range |
| --- | --- | --- |
| Copper sulfate | 4.00 | 0.5–85 |
| Zirconium sulfate solution | 5.00 | 0.5–85 |
| Ammonium hydroxide | 0.50 | 0–25 |
| Citric acid* | 3.00 | 0–35 |
| Glyoxal | 4.00 | 0.1–75 |
| Water | 83.50 | 0–80 |
| Total | 100.00 | |

*All or part of the citric acid can be replaced with sodium citrate.

Formulation Protocol:
1. To 10 mls of water add ammonium hydroxide and agitate.
2. Add to the above mixture the zirconium sulfate solution. The solution turns cloudy.
3. Add citric acid and agitate until the acid is completely dissolved and the solution is clear.
4. Add the remaining water.
5. Add the glyoxal while agitating the solution. The solution clouds momentarily until the glyoxal reacts in the formulation at which point the formula will clarify. (However, water soluble aldehydes will not cloud when added.)

The invention may be embodied in many forms without departing from the spirit or essential characteristics of the invention. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

We claim:

1. A biowaste treatment agent consisting essentially of a metal component and an aldehyde, said treatment agent lacking a surfactant;

said metal component comprising from about 0.5% to about 85.0% by weight of the treatment agent; and said aldehyde comprising about 0.1% to about 80.0% by weight of the treatment agent.

2. A biowaste treatment agent as defined in claim 1 in which the metal component is a metal source selected from the group consisting of copper, zirconium, silver, magnesium, titanium, zinc, iron, manganese, aluminum, and a mixture thereof.

3. A biowaste treatment agent as defined in claim 1 in which the metal component is selected from the group consisting of aluminum chlorohydrate, aluminum sulfate, aluminum chloride, zinc sulfate, zinc chloride, zinc acetate, copper sulfate, copper chloride, titanium sulfate, titanium trichloride, zirconium chloride, zirconium sulfate, and a mixture thereof.

4. A biowaste treatment agent as defined in claim 1 in which the aldehyde is selected from the group consisting of benzaldehyde, glyoxal, acetaldehyde, glutaraldehyde, citral, and decanal.

5. A biowaste treatment agent as defined in claim 4 in which the aldehyde is selected from the group consisting of benzaldehyde and glyoxal.

6. A biowaste treatment agent as defined in claim 5 which comprises about 5 percent of said metal component and about 4 percent of said aldehyde by weight.

7. A biowaste treatment agent as defined in claim 5 in which the metal component is aluminum chlorohydrate.

8. A biowaste treatment agent as defined in claim 5 in which the metal component is aluminum sulfate.

9. A biowaste treatment agent as defined in claim 5 in which the metal component is aluminum chloride.

10. A biowaste treatment agent as defined in claim 5 in which the metal component is zinc sulfate.

11. A biowaste treatment agent as defined in claim 5 in which the metal component is zinc chloride.

12. A biowaste treatment agent as defined in claim 5 in which the metal component is zinc acetate.

13. A biowaste treatment agent as defined in claim 5 in which the metal component is copper sulfate.

14. A biowaste treatment agent as defined in claim 5 in which the metal component is copper chloride.

15. A biowaste treatment agent as defined in claim 5 in which the metal component is titanium sulfate.

16. A biowaste treatment agent as defined in claim 5 in which the metal component is titanium trichloride.

17. A biowaste treatment agent as defined in claim 5 in which the metal component is zirconium chloride.

18. A biowaste treatment agent as defined in claim 5 in which the metal component is zirconium sulfate.

19. A biowaste treatment agent consisting essentially of a metal component and an aldehyde, said treatment agent lacking a surfactant;

said metal component comprising a metal source selected from the group consisting of copper, zirconium, silver, magnesium, titanium, zinc, iron, manganese, aluminum, and a mixture thereof, said metal component comprising from about 0.5% to about 85.0% by weight of the treatment agent; and said aldehyde comprising about 0.1% to about 80.0% by weight of the treatment agent.

20. A biowaste treatment agent as defined in claim 19 in which the metal component is selected from the group consisting of aluminum chlorohydrate, aluminum sulfate, aluminum chloride, zinc sulfate, zinc chloride, zinc acetate, copper sulfate, copper chloride, titanium sulfate, titanium trichloride, zirconium chloride, zirconium sulfate, and a mixture thereof.

21. A biowaste treatment agent as defined in claim 19 in which the aldehyde is selected from the group consisting of benzaldehyde, glyoxal, acetaldehyde, glutaraldehyde, citral, and decanal.

22. A biowaste treatment agent as defined in claim 19 in which the aldehyde is selected from the group consisting of benzaldehyde and glyoxal.

23. A biowaste treatment agent as defined in claim 22 which comprises about 5 percent of said metal component and about 4 percent of said aldehyde by weight.

24. A biowaste treatment agent as defined in claim 22 in which the metal component is aluminum chlorohydrate.

25. A biowaste treatment agent as defined in claim 22 in which the metal component is aluminum sulfate.

26. A biowaste treatment agent as defined in claim 22 in which the metal component is aluminum chloride.

27. A biowaste treatment agent as defined in claim 22 in which the metal component is zinc sulfate.

28. A biowaste treatment agent as defined in claim 22 in which the metal component is zinc chloride.

29. A biowaste treatment agent as defined in claim 22 in which the metal component is zinc acetate.

30. A biowaste treatment agent as defined in claim 22 in which the metal component is copper sulfate.

31. A biowaste treatment agent as defined in claim 22 in which the metal component is copper chloride.

32. A biowaste treatment agent as defined in claim 22 in which the metal component is titanium sulfate.

33. A biowaste treatment agent as defined in claim 22 in which the metal component is titanium trichloride.

34. A biowaste treatment agent as defined in claim 22 in which the metal component is zirconium chloride.

35. A biowaste treatment agent as defined in claim 22 in which the metal component is zirconium sulfate.

36. A biowaste treatment agent consisting essentially of a metal component and an aldehyde, said treatment agent lacking a surfactant;

said metal component comprising from about 0.5% to about 85.0% by weight of the treatment agent; and said aldehyde selected from the group consisting of benzaldehyde, glyoxal, acetaldehyde, glutaraldehyde, citral, and decanal, said aldehyde comprising about 0.1% to about 80.0% by weight of the treatment agent.

37. A biowaste treatment agent as defined in claim 36 in which the metal component is a metal source selected from the group consisting of copper, zirconium, silver, magnesium, titanium, zinc, iron, manganese, aluminum, and a mixture thereof.

38. A biowaste treatment agent as defined in claim 36 in which the metal component is a metal source selected from the group consisting of aluminum chlorohydrate, aluminum sulfate, aluminum chloride, zinc sulfate, zinc chloride, zinc acetate, copper sulfate, copper chloride, titanium sulfate, titanium trichloride, zirconium chloride, zirconium sulfate, and a mixture thereof.

39. A biowaste treatment agent as defined in claim 36 in which the aldehyde is selected from the group consisting of benzaldehyde and glyoxal.

40. A biowaste treatment agent as defined in claim 36 which comprises about 5 percent of said metal component and about 4 percent of said aldehyde by weight.

41. A biowaste treatment agent as defined in claim 39 in which the metal component is aluminum chlorohydrate.

42. A biowaste treatment agent as defined in claim 39 in which the metal component is aluminum sulfate.

43. A biowaste treatment agent as defined in claim 39 in which the metal component is aluminum chloride.

44. A biowaste treatment agent as defined in claim 39 in which the metal component is zinc sulfate.

45. A biowaste treatment agent as defined in claim 39 in which the metal component is zinc chloride.

46. A biowaste treatment agent as defined in claim 39 in which the metal component is zinc acetate.

47. A biowaste treatment agent as defined in claim 39 in which the metal component is copper sulfate.

48. A biowaste treatment agent as defined in claim 39 in which the metal component is copper chloride.

49. A biowaste treatment agent as defined in claim 39 in which the metal component is titanium sulfate.

50. A biowaste treatment agent as defined in claim 39 in which the metal component is titanium trichloride.

51. A biowaste treatment agent as defined in claim 39 in which the metal component is zirconium chloride.

52. A biowaste treatment agent as defined in claim 39 in which the metal component is zirconium sulfate.

53. A biowaste treatment agent consisting essentially of a metal component and an aldehyde, said treatment agent lacking a surfactant;

said metal component comprising a metal source selected from the group consisting of copper, zirconium, silver, magnesium, titanium, zinc, iron, manganese, aluminum, and a mixture thereof, said metal component comprising from about 0.5% to about 85.0% by weight of the treatment agent; and said aldehyde selected from the group consisting of benzaldehyde, glyoxal, acetaldehyde, glutaraldehyde, citral, and decanal, said aldehyde comprising about 0.1% to about 80.0% by weight of the treatment agent.

54. A biowaste treatment agent as defined in claim 53 in which the metal component is a metal source selected from the group consisting of aluminum chlorohydrate, aluminum sulfate, aluminum chloride, zinc sulfate, zinc chloride, zinc acetate, copper sulfate, copper chloride, titanium sulfate, titanium trichloride, zirconium chloride, zirconium sulfate, and a mixture thereof.

* * * * *